(12) United States Patent
Sengupta et al.

(10) Patent No.: US 12,357,699 B2
(45) Date of Patent: Jul. 15, 2025

(54) B-CELL IMMUNOTHERAPY IN CANCER TREATMENT

(71) Applicant: AKAMARA THERAPEUTICS, INC., Philadelphia, PA (US)

(72) Inventors: Shiladitya Sengupta, Waltham, MA (US); Aniruddha Sengupta, Delhi (IN)

(73) Assignee: Alyssum Therapeutic s, Inc., Cambridge, MA (US)

( * ) Notice: Subject to any disclaimer, the term of this patent is extended or adjusted under 35 U.S.C. 154(b) by 1199 days.

(21) Appl. No.: 17/258,610

(22) PCT Filed: Jul. 10, 2019

(86) PCT No.: PCT/US2019/041237
§ 371 (c)(1),
(2) Date: Jan. 7, 2021

(87) PCT Pub. No.: WO2020/014387
PCT Pub. Date: Jan. 16, 2020

(65) Prior Publication Data
US 2021/0275677 A1    Sep. 9, 2021

Related U.S. Application Data

(60) Provisional application No. 62/695,946, filed on Jul. 10, 2018.

(51) Int. Cl.
| | |
|---|---|
| A61K 47/55 | (2017.01) |
| A61K 39/00 | (2006.01) |
| A61K 39/395 | (2006.01) |
| A61K 45/06 | (2006.01) |
| A61K 47/54 | (2017.01) |
| A61P 35/00 | (2006.01) |
| C07K 16/28 | (2006.01) |

(52) U.S. Cl.
CPC ........ *A61K 47/551* (2017.08); *A61K 39/3955* (2013.01); *A61K 45/06* (2013.01); *A61K 47/554* (2017.08); *A61P 35/00* (2018.01); *C07K 16/2818* (2013.01); *A61K 2039/505* (2013.01); *A61K 2039/585* (2013.01)

(58) Field of Classification Search
CPC ................ A61K 47/551; A61K 47/554; A61K 39/3955; A61K 45/06; A61K 2039/505; A61K 2039/585; A61P 35/00; C07K 16/2818
See application file for complete search history.

(56) References Cited

U.S. PATENT DOCUMENTS

2016/0145284 A1    5/2016   Sengupta et al.

FOREIGN PATENT DOCUMENTS

| WO | WO-2015153345 A1 * | 10/2015 | ........... A61K 31/282 |
| WO | WO-2018126259 A1 * | 7/2018 | ............... A61P 35/00 |

OTHER PUBLICATIONS

He et al (Year: 2016).*
Denkert et al., Tumor-Inflictrating Lymphocytes and Response to Neoadjuvant Chemotherapy With or Without Carboplatin in Human Epidermal Growth Factor Receptor 2-Positive and Triple-Negative Primary Breast Cancers, Mar. 20, 2015, 983-991, 33 / 9.
Dilillo et al., B Cells Are Required For Optimal CD4+ and CD8+ T Cell Tumor Immunity: Therapeutic B Cell Depletion Enhances B16 Melanoma Growth in Mice, Journal of Immunology, 2010; 184:4006-4016.
Harris and Drake, Primer on tumor immunology and cancer immunotherapy, Journal for Immunotherapy, Journal for ImmunoTherapy of Cancer, 2013, 1:12, pp. 1-9.
Harris et al., Reciprocal regulation of polarized cytokine production by effector B and T cells, Nature Immunology, 2000; 1:475-482.
Hodi et al., Improved Survival With Ipilimumab in Patients With Metastatic Melanoma, N England Journal of Medicine, Med 2010; 363:711-723.
Li et al., In vivo sensitized and in vitro activated B cells mediate tumor regression in cancer adoptive immunotherapy, Journal of Immunology, 2009; 183:3195-3203).
Mellman et al., Cancer immunotherapy comes of age, Nature 2011;480:480-489.
Patel et al., Clinical cancer advances 2013: annual report on progress against cancer from the American Society of Clinical Oncology, J Clinical Oncology, 2014; 32:129-160.
Postow et al., Immune checkpoint blockade in cancer therapy, J Clinical Oncology, 2015; 33:1974-1982.
Sorrentino et al., B cells contribute to the antitumor activity of CPG-oligodeoxynucleotide in a mouse model metastatic lung carcinoma, American Journal of Respiratory and Critical Care Medicine, 2011; 183: 1369-1379.
Tsushima et al., Predominant expression of B7-H1 and its immunoregulatory roles in oral squamous cell carcinoma, Oral Oncol. 2006; 42:268-274.
Voena et al., Advances in cancer immunology and cancer immunotherapy, Discov Med 2016; 21:125-133.
Whiteside TL, Immune suppression in cancer: effects on immune cells, mechanisms and future therapeutic intervention, Seminars in Cancer Biology, 2006; 16:3-15.

(Continued)

*Primary Examiner* — Jeffrey S Lundgren
*Assistant Examiner* — Ibrahim D Bori
(74) *Attorney, Agent, or Firm* — BakerHostetler

(57) ABSTRACT

The present disclosure provides methods for treating cancer in a patient, comprising administering to the patient (i) a therapeutically effective amount of a compound of formula (VIII), or a pharmaceutically acceptable salt thereof, wherein Q, linker, and lipid are defined herein, and (ii) a therapeutically effective amount of an immune checkpoint inhibitor. Q-linker-lipid (VIII) In some embodiments, the compound is the following structure (10-125), or a pharmaceutically acceptable salt thereof: Pharmaceutical compositions comprising a compound of formula (VIII), such as 10-125, or a pharmaceutically acceptable salt thereof, an immune checkpoint inhibitor, and a pharmaceutically acceptable excipient are also described.

14 Claims, 9 Drawing Sheets

(56) References Cited

OTHER PUBLICATIONS

Wolchok et al., Ipilimumab monotherapy in patients with pretreated advanced melanoma: a randomised, double-blind multicentre, phase 2, dose-ranging study, Lancet Oncol 2010; 11:155-164.
Zeng et al., JAMA Oncol. 2015; 1:88-96.

* cited by examiner

A

| Group | Mice per group | Compound (dose mg/kg) |
|---|---|---|
| 1 | 6 | Saline (b5d x 2; equivalent volume) |
| 2 | 8 | IO-125 (20 mgPt/kg; b5d x 2) |
| 3 | 8 | anti-PD1 antibody (2 mg/kg; q3d x 2) |
| 4 | 9 | IO-125 + anti-PD1 antibody (20 mgPt/kg; b5d x 2) + (2 mg/kg; q3d x 2) |

B

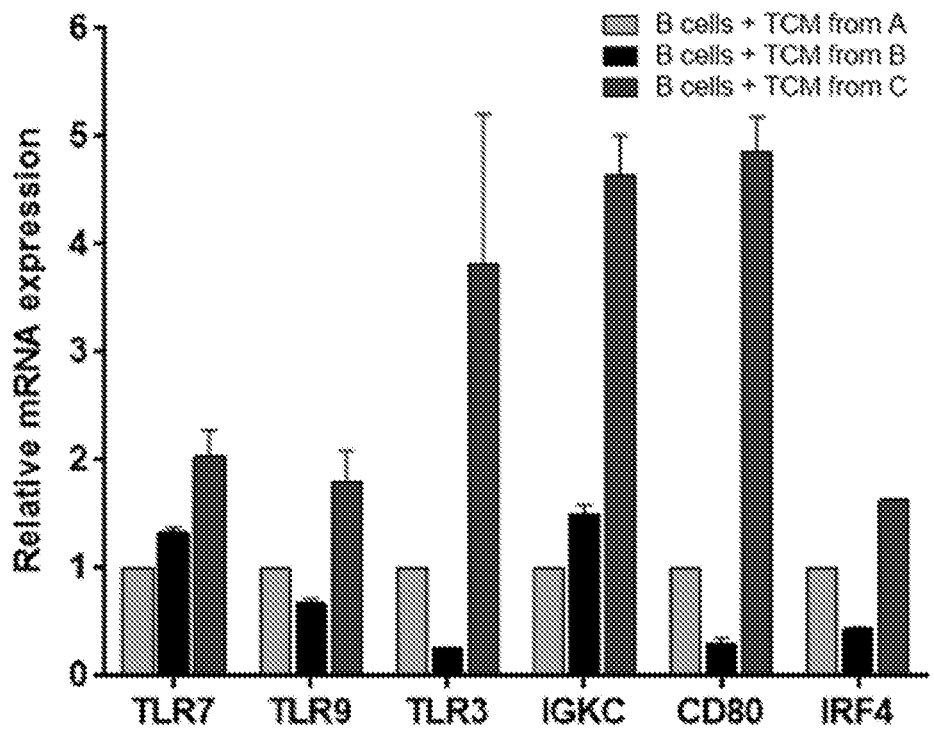
Figure 4B
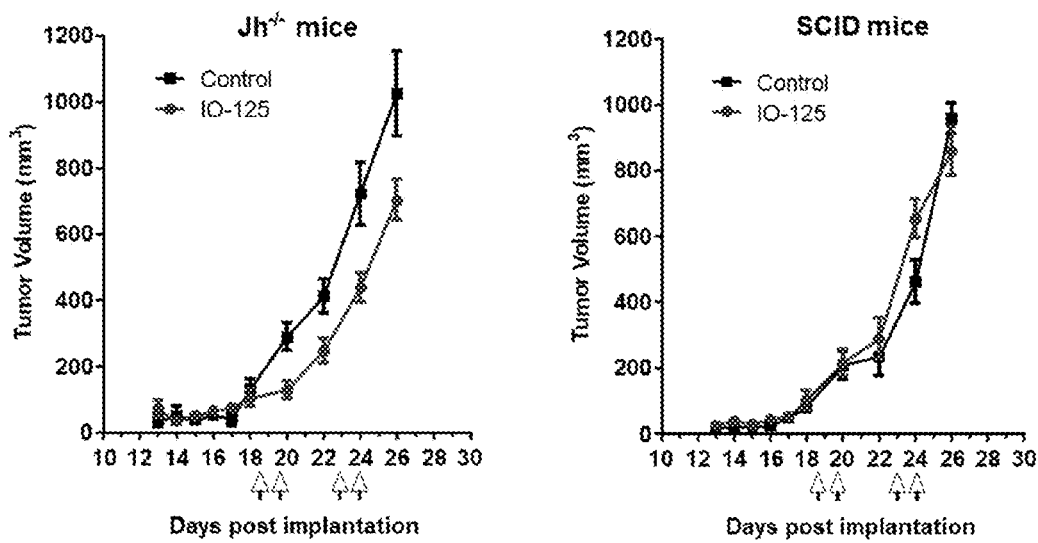
Figure 4C                    Figure 4D

B-CELL IMMUNOTHERAPY IN CANCER TREATMENT

CROSS-REFERENCE TO RELATED APPLICATIONS

This application is a U.S. National Stage of International Patent Application No. PCT/US2019/041237 filed Jul. 10, 2019, which claims the benefit of U.S. Provisional Patent Application No. 62/695,946, filed Jul. 10, 2018, which are both incorporated by reference herein.

TECHNICAL FIELD

This disclosure relates to methods and pharmaceutical compositions for treating cancer.

BACKGROUND

Cancer cells have the ability to bind receptors on immune cells and evade immune surveillance through inhibitory signalling pathways or immune-inhibitory checkpoint proteins. The suppression of these inhibitory proteins can enhance immune responses and prevent cancer progression. Studies have improved therapeutic approaches, leading to development of immunotherapy as an elegant approach to cancer treatment through activation of the immune system against cancer.

Immunotherapy is currently used to treat both solid and hematological malignancies, showing significant increase in patient survival and helping us understand how immunity and immunosuppression regulate tumor growth. The goal of immunotherapy is to activate the patient's own immune system to eliminate cancer, with high selectivity, low toxicity, and durable response. Numerous immune checkpoint proteins are dysregulated in tumors and immune cells, contributing to immune evasion. Blocking these inhibitory checkpoint proteins has been used as a strategy to enhance T-cell infiltration and effector functions in cancer. Blocking antibodies against the T-cell coinhibitory receptors or ligands, such as CTLA-4, PD-1, and PD-L1, have shown promising efficacy in numerous cancers.

New methods and pharmaceutical formulations for treating patients with cancer are needed.

SUMMARY

The present disclosure provides methods for treating cancer in a patient. The methods comprise administering to the patient (i) a therapeutically effective amount of a compound of formula (VIII), or a pharmaceutically acceptable salt thereof, Q-linker-lipid (VIII), wherein Q, linker, and lipid are defined herein; and (ii) a therapeutically effective amount of an immune checkpoint inhibitor. In some embodiments, the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

The present disclosure also provides methods for treating cancer in a patient. The methods comprise administering to the patient (i) a therapeutically effective amount of a compound of the following structure (IO-125), or a pharmaceutically acceptable salt thereof:

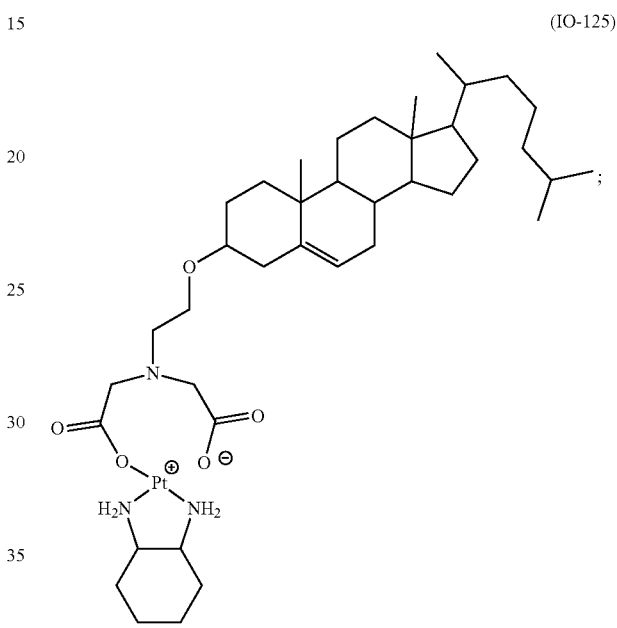

(IO-125)

and (ii) a therapeutically effective amount of an immune checkpoint inhibitor. In some embodiments, the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

The present disclosure further provides pharmaceutical compositions that comprise (i) a compound of formula (VIII), or a pharmaceutically acceptable salt thereof: Q-linker-lipid (VIII), wherein Q, linker, and lipid are defined herein: (ii) an immune checkpoint inhibitor; and (iii) a pharmaceutically acceptable excipient. In some embodiments, the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

The present disclosure also provides pharmaceutical compositions that comprise (i) a compound of the following structure (IO-125), or a pharmaceutically acceptable salt thereof:

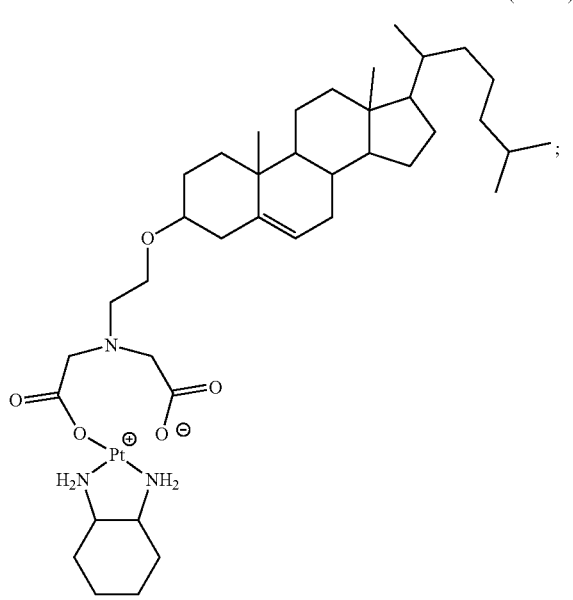

(ii) an immune checkpoint inhibitor; and (iii) a pharmaceutically acceptable excipient. In some embodiments, the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

Other aspects and embodiments of the invention will be readily apparent from the following detailed description of the invention.

DETAILED DESCRIPTION OF THE DRAWINGS

The present application is further understood when read in conjunction with the appended drawings. For the purpose of illustrating the subject matter, there are shown in the drawings exemplary embodiments of the subject matter: however, the presently disclosed subject matter is not limited to the specific compositions, methods, devices, and systems disclosed. In addition, the drawings are not necessarily drawn to scale.

FIG. 4B is a bar graph examining B cell differentiation and TLR activation markers, through evaluation of relative mRNA profile in B-cells treated with conditioned media from 4T1 cells. Results indicate that B cell differentiation markers and TLR activation markers were substantially increased in splenic B cells cultured with TCM from IO-125 treated 4T1 cells. All values are normalized to splenic B cells treated with 4T1 conditioned media.

FIGS. 4C and 4D are graphs for tumor growth in immunodeficient mice, i.e., $Jh^{-/-}$ mice (4C) and SCID mice (4D) after implantation and treatment with IO-125. Tumors do not regress in mice lacking immune cells.

Figure 5A:
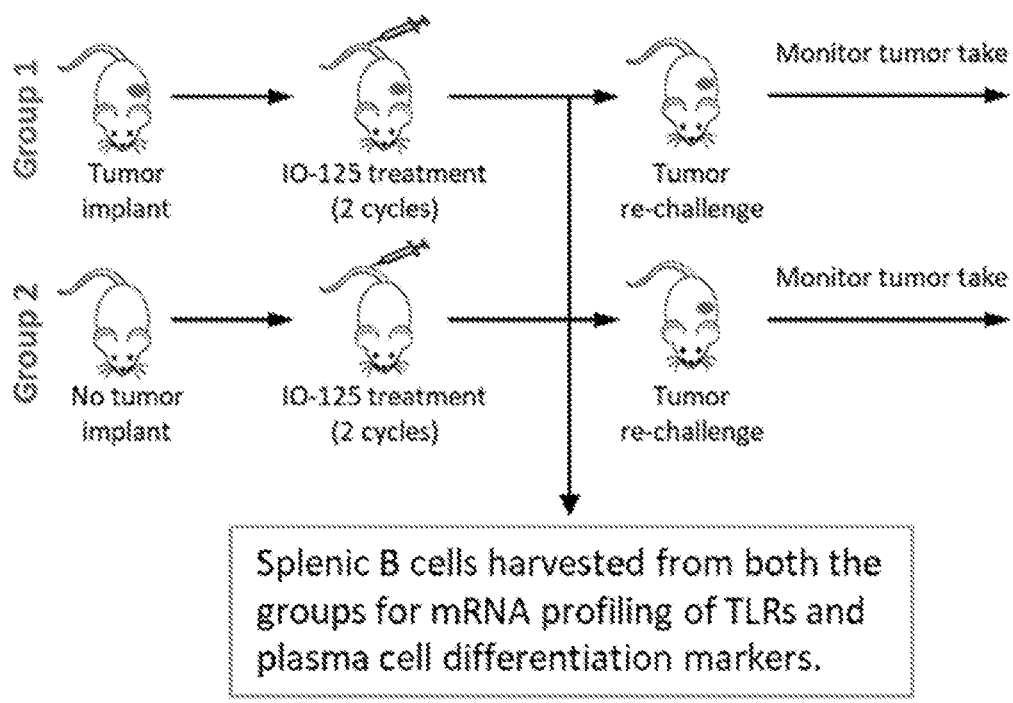

FIG. 5A is a schematic representation depicting harvest and study of splenic B-cells.

Figure 5B:
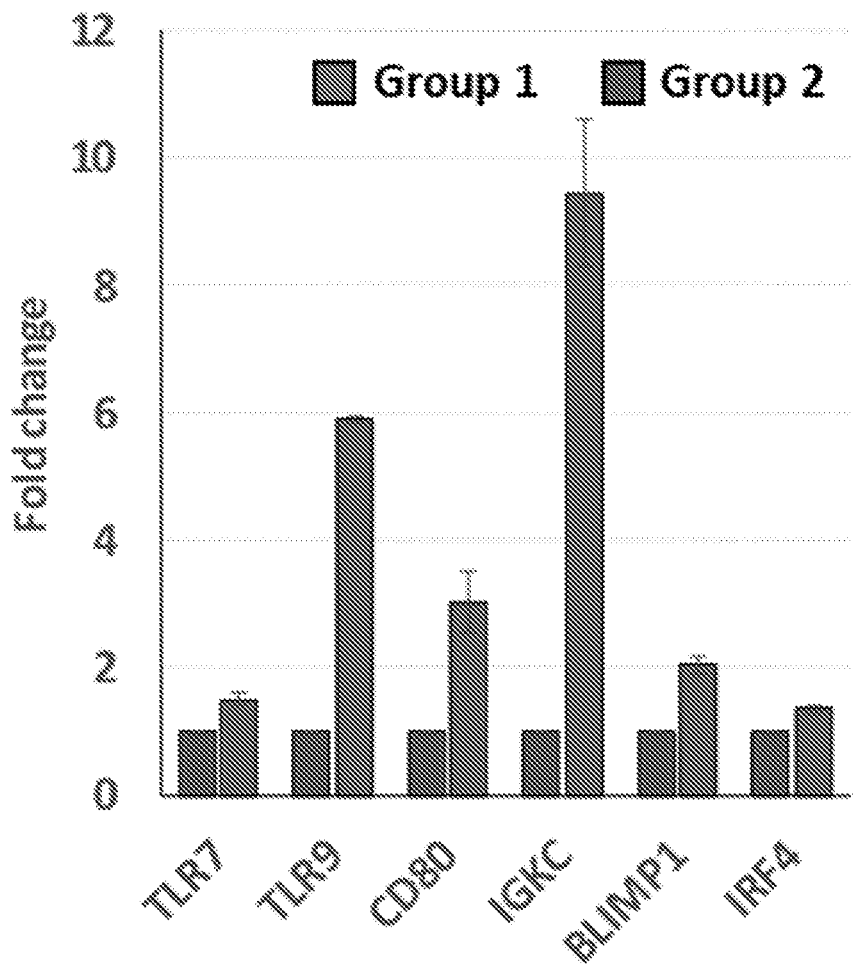

FIG. 5B is a bar graph showing plasma B cell differentiation and TLR activation markers by evaluating their relative mRNA profile in treated tumors. Results indicate significant increase in B cell differentiation markers and TLR activation markers in splenic B cells isolated from tumor bearing mice treated with IO-125. All values are normalized to splenic B cells isolated from Group 2 mice.

Figure 5C:
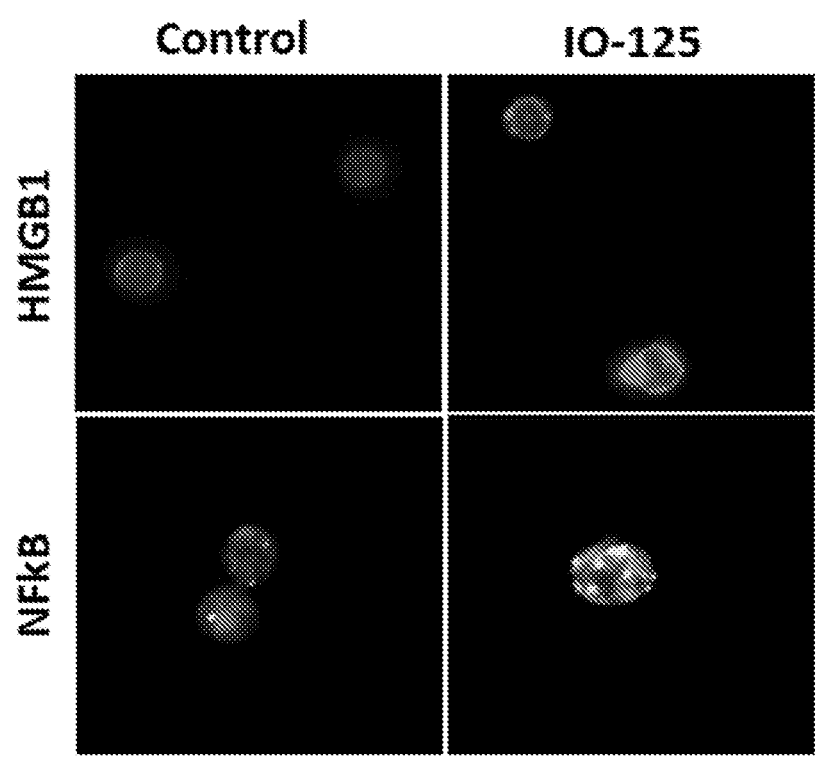

FIG. 5C depicts immunofluorescence imaging showing clustering of HMGB1 and nuclear translocation of NF-kB in B cells isolated from Group 1 animals.

DETAILED DESCRIPTION

In the disclosure, the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A." "B." "C." "A or B." "A or C." "B or C." or "A. B. or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude an optional element. As such, this statement is intended to serve as antecedent basis for use of such exclusive terminology as "solely." "only" and the like in connection with the recitation of claim elements, or use of a "negative" limitation. Finally, while an embodiment may be described as part of a series of steps or part of a more general structure, each said step may also be considered an independent embodiment in itself.

The present disclosure provides methods of treating cancer using a small molecule, i.e., a compound of formula (VIII) Q-linker-lipid (VIII), wherein Q is a platinum containing moiety and the linker has at least one linkage to the platinum atom, such as IO-125, and an immune checkpoint inhibitor. As shown herein, the compounds of formula (VIII), including IO-125, demonstrate remarkable anti-cancer activity and inhibition, i.e., anti-tumor activity or tumor growth inhibition, when administered with immune checkpoint inhibitors. This activity was found to be appreciable across a number of cancer lines in different preclinical tumor models. In fact, IO-125 synergized with immune checkpoint inhibitor, resulting in improved tumor regression.

In some aspects, Q is

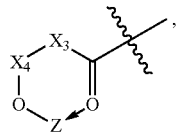

wherein, $X_3$ is $(CH_2)_n$, $CH_2$—NH, or $C_4H_8$; $X_4$ is CO or —CH—CH$_3$; Z is a platinum containing compound, wherein the platinum forms a part of the ring; and n is 0, 1, or 2. In some embodiments, $X_3$ is $(CH_2)$ n. In other embodiments, $X_3$ is $CH_2$—NH. In further embodiments, $X_3$ is $C_4H_8$. In yet other embodiments, $X_4$ is CO. In still further embodiments, $X_4$ is —CH—CH$_3$. In other embodiments, n is 0. In further embodiments, n is 1. In still other embodiments, n is 2.

In other aspects, Q is

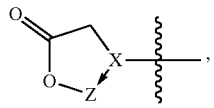

wherein, X is NH or N ($CH_2COO^-$); and Z is a platinum containing compound, wherein the platinum forms a part of the ring. In some embodiments, X is NH. In other embodiments, X is N ($CH_2COO^-$).

In further aspects, Q is

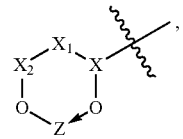

wherein, X is $S^+$, C, $S^+$=O, $N^+H$, or P=O; $X_1$ is —CH, —CH$_2$ or —CH$_2$O; $X_2$ is C=O; and Z is a platinum containing compound, wherein the platinum forms a part of the ring. In some embodiments, X is $S^+$. In other embodiments, X is C. In further embodiments, X is $S^+$=O. In still other embodiments, X is $N^+H$. In yet further embodiments, X is P=O. In some embodiments, $X_1$ is —CH. In other embodiments, $X_1$ is —CH$_2$. In further embodiments, $X_1$ is —CH$_2$O.

In yet other aspects, Q is

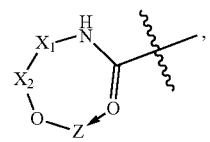

wherein, $X_1$ is $(CH_2)_n$; $X_2$ is C=O; Z is a platinum containing compound, wherein the platinum forms a part of the ring; and n is 0, 1, or 2. In some embodiments, n is 0. In other embodiments, n is 1. In further embodiments, n is 2.

In some embodiments of the various aspects disclosed herein, the platinum is coordinated to a leaving group via a unique O—Pt monocarboxylato covalent bond and a =O→Pt coordinate bond. Further, the present disclosure also discloses platinum based compounds wherein the platinum is coordinated to a leaving group via O—Pt monocarboxylato or dicarboxylato covalent bond(s). In other embodiments, the platinum moiety is a platinum (II) or platinum (IV) compound. In further embodiments, the platinum (II) compound is DACH-platinum, cisplatin, oxaliplatin, carboplatin, paraplatin, sartraplatin, or combinations thereof. In other embodiments, the platinum containing compound is a Pt (II) compound, Pt (IV) compound or halide containing platinum compound. In a preferred embodiment, the platinum compound is oxaliplatin.

In some aspects, Z is

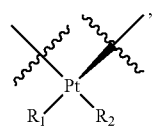

wherein, $R_1$ and $R_2$ are, independently, halogen, alkyl, amino, alkylamino, dialkylamino, hydroxyl, alkoxy, thiol, thioalkyl, O-acyl, or combinations thereof. In some embodiments, $R_1$ and $R_2$, together with the Pt atom form an optionally substituted cyclyl or heterocyclyl.

In other aspects, Z is

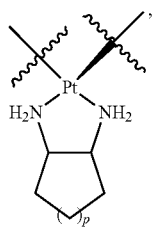

wherein, p is 0, 1, 2, or 3. In some embodiments, p is 0. In other embodiments, p is 1. In further embodiments, p is 2. In yet other embodiments, p is 3.

In other aspects, Z is

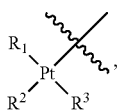

wherein, $R_1$, $R_2$ and $R_3$ are, independently, halogen, alkyl, amino, alkylamino, dialkylamino, hydroxyl, alkoxy, thiol, thioalkyl, O-acyl, -linker-lipid, or combinations thereof. In some embodiments, $R_1$ and $R_2$ together with the Pt atom or $R_2$ and $R_3$ together with the Pt atom form an optionally substituted cyclyl or heterocyclyl. In other embodiments, $R_1$ and $R_2$ together with the Pt atom and $R_2$ and $R_3$ together with the Pt atom form an optionally substituted cyclyl or heterocyclyl.

In further aspects, Z is

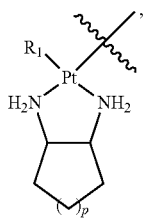

wherein, $R_1$ is halogen, alkyl, amino, alkylamino, dialkylamino, hydroxyl, alkoxy, thiol, thioalkyl, O-acyl, or combinations thereof; and p is 0, 1, 2, or 3. In some embodiments, $R_1$ is halogen —Cl, —NCS, —O=S(CH$_3$)$_2$, —SCH$_3$, or -linker-lipid. In other embodiments, p is 2.

In yet other aspects, Z is

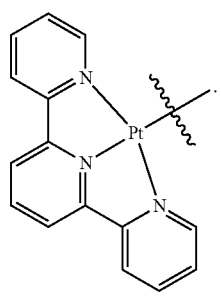

In still further aspects, Z is

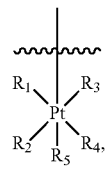

wherein, $R_1$, $R_2$, $R_3$, $R_4$ and $R_5$ are, independently, halogen, alkyl, amino, alkylamino, dialkylamino, hydroxyl, alkoxy, thiol, thioalkyl, O-acyl, -linker-lipid, or combinations thereof. In some embodiments, $R_1$ and $R_2$ together with the Pt atom form an optionally substituted cyclyl or heterocyclyl. In other embodiments, $R_1$ and $R_2$ together with the Pt atom form an optionally substituted cyclyl or heterocyclyl. In yet further embodiments, $R_1$ and $R_2$ together with the Pt atom form an optionally substituted cyclyl or heterocyclyl and $R_3$ and $R_4$ together with the Pt atom form an optionally substituted cyclyl or heterocyclyl. In still other embodiments, $R_5$ is OH, OC(O)CH$_3$, or OC(O)-phenyl.

In other aspects, Z is

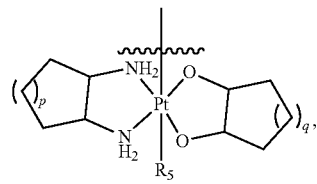

wherein, p and q are, independently, 0, 1, 2, or 3. In some embodiments, p is 2. In other embodiments, q is 2. In further embodiments, p and q are both 2.

In further aspects, Z is

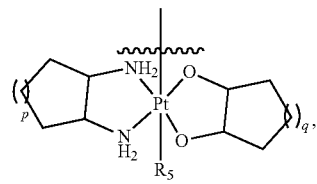

wherein, p and q are both 2; and $R_5$ is OH, OC(O)CH$_3$, or OC(O)-phenyl.

In some embodiments, the platinum (II) compound comprises at least two nitrogen atoms, where said nitrogen atoms are directly linked to platinum. In a further embodiment, the two nitrogen atoms are linked to each other via an optionally substituted linker, e.g. acyclic or cyclic linker. The term "cyclic linker" refers to a linking moiety that comprises at least one ring structure. Examples of cyclic linkers include, without limitation, aryl, heteroaryl, cyclyl or heterocyclyl.

In some aspects, Q is

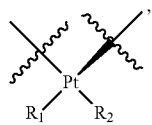

wherein, $R_1$ and $R_2$ are, independently, halogen, alkyl, amino, alkylamino, dialkylamino, hydroxyl, alkoxy, thiol, thioalkyl, O-acyl, or any combinations thereof. In some embodiments, $R_1$ and $R_2$, together with the Pt atom form an optionally substituted cyclyl or heterocyclyl.

In other aspects, Q is

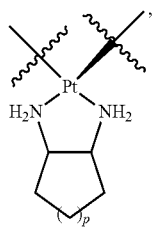

wherein, p is 0, 1, 2, or 3. In some embodiments, p is 2.

In further aspects, Q is

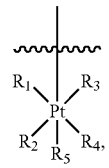

wherein, $R_1$, $R_2$ and $R_3$ are, independently, halogen, alkyl, amino, alkylamino, dialkylamino, hydroxyl, alkoxy, thiol, thioalkyl, O-acyl, or combinations thereof. In some embodiments, $R_1$ and $R_2$ together with the Pt atom or $R_2$ and $R_3$ together with the Pt atom form an optionally substituted cyclyl or heterocyclyl. In other embodiments, $R_1$ and $R_2$ together with the Pt atom and $R_2$ and $R_3$ together with the Pt atom form an optionally substituted cyclyl or heterocyclyl.

In yet other aspects, Q is

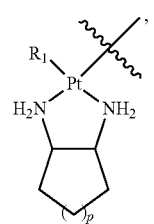

wherein, $R_1$ is halogen, alkyl, amino, alkylamino, dialkylamino, hydroxyl, alkoxy, thiol, thioalkyl, O-acyl, or combinations thereof; and p is 0, 1, 2, or 3. In some embodiments, $R_1$ is halogen —Cl, —NCS, —O—S(CH$_3$)$_2$, —SCH$_3$, or -linker-lipid. In other embodiments, p is 2.

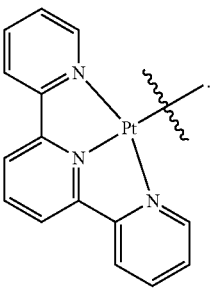

In still further aspects, Q is

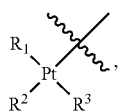

In other aspects, Q is wherein, $R_1$, $R_2$, $R_3$, $R_4$ and $R_5$ are, independently, halogen, alkyl, amino, alkylamino, dialkylamino, hydroxyl, alkoxy, thiol, thioalkyl, O-acyl, or combinations thereof. In some embodiments, $R_1$ and $R_2$ together with the Pt atom form an optionally substituted cyclyl or heterocyclyl. In other embodiments, $R_1$ and $R_2$ together with the Pt atom form an optionally substituted cyclyl or heterocyclyl. In further embodiments, $R_1$ and $R_2$ together with the Pt atom form an optionally substituted cyclyl or heterocyclyl and $R_3$ and $R_4$ together with the Pt atom form an optionally substituted cyclyl or heterocyclyl. In still other embodiments, $R_5$ is OH, OC(O)CH$_3$, or OC(O)-phenyl.

In further aspects, Q is

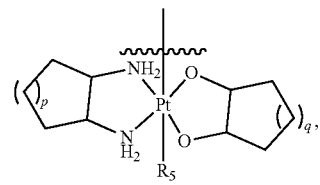

wherein, p and q are, independently, 0, 1, 2, or 3. In some embodiments, p is 2. In other embodiments, q is 2. In further embodiments, p and q are both 2.

In further aspects, Q is

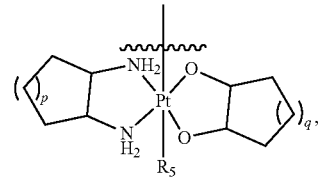

wherein, p and q are both 2; and $R_5$ is OH, OC(O)CH$_3$, or OC(O)-phenyl.

The term "lipid" as used herein is used in the conventional sense and includes compounds of varying chain length, from as short as about 2 carbon atoms to as long as about 28 carbon atoms. The compounds are saturated or unsaturated, in the form of straight- or branched-chains, or in the form of unfused or fused ring structures. Exemplary lipids include, but are not limited to, a fat, wax, sterol, steroid, bile acid, fat-soluble vitamin (such as A, D, E, and K), monoglyceride, diglyceride, phospholipid, glycolipid, sulpholipid, amino-lipid, chromolipid (lipochrome), glycerophospholipid, sphingolipid, prenollipid, saccharolipid, polyketide, or fatty acid. In some embodiments, the lipid is a sterol lipid, fatty acid, fatty alcohol, glycerolipid (e.g., monoglyceride, diglyceride, or triglyceride), phospholipid, glycerophospholipid, sphingolipid, prenol lipid, saccharolipid, polyketide, or any combination thereof. In other embodiments, the lipid is a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. In further embodiments, the lipid is a highly unsaturated fatty acid or alcohol. The term "highly polyunsaturated fatty acid" or "highly polyunsaturated fatty alcohol" as used herein refers to a fatty acid or alcohol having at least 18 carbon atoms and at least 3 double bonds. In yet other embodiments, the lipid is an omega-3 fatty acid. The term "omega-3 fatty acid" as used herein refers to a polyunsaturated fatty acid, where the first double bond occurs at the third carbon-carbon bond from the end opposite the acid group.

In some preferred embodiments, the lipid is 1,3-propanediol dicaprylate/dicaprate; 10-undecenoic acid; 1-dotriacontanol; 1-heptacosanol; 1-nonacosanol; 2-ethyl hexanol; an androstane; arachidic acid; arachidonic acid; arachidyl alcohol; behenic acid; behenyl alcohol; Capmul MCM $C_{10}$; capric acid; capric alcohol; capryl alcohol; caprylic acid; caprylic/capric acid ester of saturated fatty alcohol $C_{12}$-$C_{18}$; caprylic/capric triglyceride; caprylic/capric triglyceride; ceramide phosphorylcholine (Sphingomyelin, SPH); ceramide phosphorylethanolamine (Sphingomyelin, Cer-PE); ceramide phosphorylglycerol; ceroplastic acid; cerotic acid; cerotic acid; ceryl alcohol; cetearyl alcohol; Ceteth-10; cetyl alcohol; a cholane; a cholestane; cholesterol; cis-11-eicosenoic acid; cis-11-octadecenoic acid; cis-13-docosenoic acid; cluytyl alcohol; coenzyme Q10 (CoQ10); dihomo-γ-linolenic; docosahexaenoic acid; egg lecithin; eicosapentaenoic acid; eicosenoic acid; elaidic acid; elaidolinolenyl alcohol; elaidolinoleyl alcohol; elaidyl alcohol; erucic acid; erucyl alcohol; estranes; ethylene glycol distearate (EGDS); geddic acid; geddyl alcohol; glycerol distearate (type I) EP (Precirol ATO 5); glycerol tricapry late/caprate; glycerol tricapry late/caprate (CAPTEX® 355 EP/NF); glyceryl monocaprylate (Capmul MCM C8 EP); glyceryl triacetate; glyceryl tricaprylate; glyceryl tricapry late/caprate/laurate; glyceryl tricapry late/tricaprate; glyceryl tripalmitate (Tripalmitin); henatriacontylic acid; heneicosyl alcohol; heneicosylic acid; heptacosylic acid; heptadecanoic acid; heptadecyl alcohol; hexatriacontylic acid; isostearic acid; isostearyl alcohol; lacceroic acid; lauric acid; lauryl alcohol; lignoceric acid; lignoceryl alcohol; linoelaidic acid; linoleic acid; linolenyl alcohol; linoleyl alcohol; margaric acid; mead; melissic acid; melissyl alcohol; montanic acid; montanyl alcohol; myricyl alcohol; myristic acid; myristoleic acid; myristyl alcohol; neodecanoic acid; neoheptanoic acid; neononanoic acid; nervonic; nonacosylic acid; nonadecyl alcohol; nonadecylic acid; nonadecylic acid; oleic acid; oleyl alcohol; palmitic acid; palmitoleic acid; palmitoleyl alcohol; pelargonic acid; pelargonic alcohol; pentacosylic acid; pentadecyl alcohol; pentadecylic acid; phosphatidic acid (phosphatidate, PA); phosphatidylcholine (lecithin, PC); phosphatidylethanolamine (cephalin, PE); phosphatidylinositol (PI); phosphatidylinositol bisphosphate (PIP2); phosphatidylinositol phosphate (PIP); phosphatidylinositol triphosphate (PIP3); phosphatidylserine (PS); polyglyceryl-6-distearate; a pregnane; propylene glycol dicaprate; propylene glycol dicaprylocaprate; propylene glycol dicaprylocaprate; psyllic acid; recinoleaic acid; recinoleyl alcohol; sapienic acid; soy lecithin; stearic acid; stearidonic; stearyl alcohol; tricosylic acid; tridecyl alcohol; tridecylic acid; triolein; undecyl alcohol; undecylenic acid; undecylic acid; vaccenic acid; α-linolenic acid; γ-linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, γ-linolenic acid; or any combination thereof. In some embodiments, the lipid is cholesterol or alpha tocopherol.

As used herein, the term "linker" means an organic moiety that connects two parts of a compound. Linkers typically comprise a direct bond or an atom such as oxygen or sulfur, a unit such as $NR^1$, C(O), C(O)NH, C(O)O, NHC(O)O, OC(O)O, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $NR^1$, C(O), C(O)NH, C(O)O, NHC(O)O, OC(O)O, $SO_2NH$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S-, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

Linkers according to the present invention include moieties comprising two or more carbon molecules such as, for example, ethylenediamine, ethyleneglycol, glycine, beta-alanine and polyethylene glycol (PEG) of molecular weight about 44 to about 200 kD. Further, it is to be understood from the present disclosure that the platinum moiety and/or the lipid may be modified to comprise functional groups for linking to the linker molecule.

In some embodiments, the linker is —X—CH$_2$—X$_2$—X$_1$—, wherein X is NH; X$_1$ is C(O)O, C(O)NH, O(CH$_2$)—O, NH, or O; X$_2$ is (CH$_2$)n or C(O); and n is 0, 1, 2, 3, 4, or 5. In other embodiments, the linker is —(CH$_2$)$_n$O—, —(CH$_2$)$_n$NHC(O)O—, —(CH$_2$)$_n$OC(O)NH—, —(CH$_2$)$_n$C(O)NH(CH$_2$)$_m$O—, —(CH$_2$)$_n$O(CH$_2$)$_m$O—, —(CH$_2$)$_n$O(O)-, —(CH$_2$)$_n$NHC(O)(CH$_2$)$_m$O—, or —(CH$_2$)$_n$C(O)O—; and n and m are independently 0, 1, 2, 3, 4, or 5. In further embodiments, the linker is —X$_3$—X$_4$X$_5$-X$_6$—, wherein X$_3$ is CH, CH$_2$, or O; and X$_4$, X$_5$ and X$_6$ are independently same or different and are —CH$_2$O— or O. In yet other embodiments, the linker is —CH$_2$O—. In still further embodiments, the linker is a bond, —O—, NHCH$_2$CH$_2$NHC(O)—, —NHCH$_2$CH$_2$NHC(O)O—, —NHCH$_2$CH$_2$—, —NHCH$_2$CH$_2$O—, —NHCH$_2$C(O)—, —NHCH$_2$C(O)O—, —NHCH$_2$C(O)OCH$_2$CH$_2$CH$_2$—, —NHCH$_2$C(O)OCH$_2$CH$_2$CH$_2$O—, —NHCH$_2$C(O)NH—, —CH$_2$CH$_2$—, —CH$_2$CH$_2$O—, —CH$_2$CH$_2$NHC(O)—, —CH$_2$CH$_2$NHC(O)O—, —CH$_2$CH$_2$O—, —CH$_2$C(O)NHCH$_2$CH$_2$—, —CH$_2$C(O)NHCH$_2$CH$_2$O—, —CH$_2$CH$_2$OCH$_2$CH$_2$—, —CH$_2$CH$_2$OCH$_2$CH$_2$O—, —CH$_2$C(O)—, —CH$_2$C(O)O—, —CH$_2$CH$_2$CH$_2$—, —CH$_2$CH$_2$CH$_2$O—, =CH—CH=CH$_2$—, =CH—CH=CHCH$_2$O—, —CH=CHCH$_2$—, —CH=CHCH$_2$O—, —OCH$_2$CH$_2$O—, —CH$_2$—, —CH$_2$O—, —NHC(O)CH$_2$—, —NHC(O)CH$_2$O—, —C(O)CH$_2$—, —C(O)CH$_2$O—, —OC(O)CH$_2$—, —OC(O)CH$_2$O—, —C(O)CH$_2$CH$_2$C(O)NHCH$_2$CH$_2$—, —OC(O)CH$_2$CH$_2$C(O)NHCH$_2$CH$_2$—, —C(O)CH$_2$CH$_2$C(O)NHCH$_2$CH$_2$O—, —OC(O)CH$_2$CH$_2$C(O)NHCH$_2$CH$_2$O—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —NHCH$_2$CH$_2$NHC(O)O—, or combinations thereof.

In some embodiments, the platinum based compounds are of Formula (I), wherein, X is NH; X$_1$ is COOH, CONH$_2$, O—(CH$_2$)$_n$—OH, NH$_2$ or OH; X$_2$ is (CH$_2$)$_n$ or CO; X$_3$ is (CH$_2$)$_n$, CH$_2$—NH, or C$_4$H$_8$; X$_4$ is CO or —CH—CH$_3$; Z is a platinum containing compound, wherein the platinum forms a part of Formula I ring; and n is 0, 1, or 2.

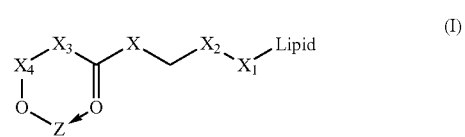

(I)

In other embodiments, the platinum based compounds are of Formula (II), wherein, X is NH or N—$CH_2COO^-$; $X_1$ is —$(CH_2)_nOH$, —$(CH_2)_nNHCOOH$, —$(CH_2)_nCONH(CH_2)_n$ OH, $(CH_2)_nO(CH_2)_nOH$, $(CH_2)_nC$=O, —$(CH_2)_nNHCO$ $(CH_2)_nOH$ and $(CH_2)_n$—COOH; Z is platinum containing compound, wherein the platinum forms a part of Formula II ring; and n is 0, 1, or 2.

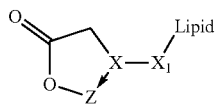
(II)

In further embodiments, the platinum based compounds are represented of Formula (III), wherein, X is $S^+$, C, $S^+$=O, $N^+H$, or P=O; $X_1$ is —CH, —$CH_2$ or —$CH_2O$; $X_2$ is C=O; $X_3$ is CH, $CH_2$ or O; $X_4$, $X_5$, and $X_6$ are, independently, —$CH_2O$ or O; Z is platinum containing compound, wherein the platinum forms a part of Formula III ring.

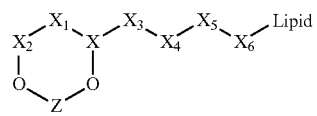
(III)

In yet other embodiments, the platinum based compounds are of Formula (IV), wherein, X is $CH_2OH$; $X_1$ is $(CH_2)_n$; $X_2$ is C=O; Z is platinum containing compound, wherein the platinum forms a part of Formula IV ring; and n is 0, 1, or 2.

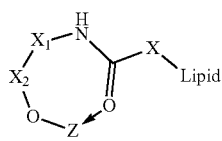
(IV)

In some aspects, the compound of formula (VIII) is IO-125. As used herein, the term "IO-125" refers to a compound having the following structure:

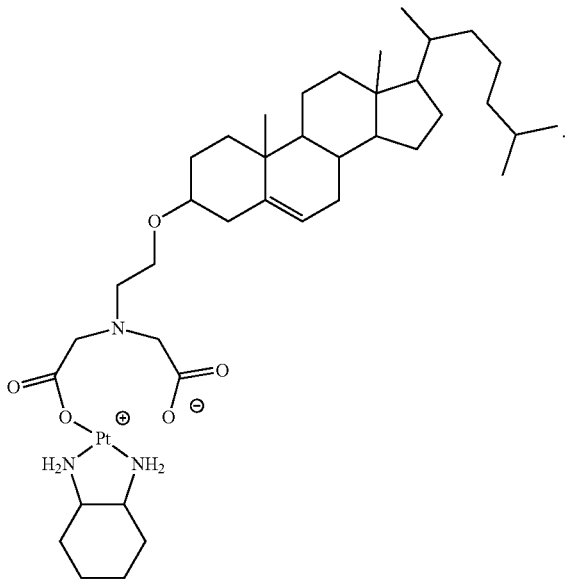
(IO-125)

The compound of formula (VIII), including IO-125, may also refer to any isomers thereof. As used herein, "isomer" refers to a compound having the same molecular formula, but different sequence of bonding or arrangement of the atoms. In some embodiments, the isomers are stereoisomers.

In some embodiments, the isomer includes one or more asymmetric centers, i.e., chiral centers, and thus includes diastereoisomers and enantiomers. The term "diastereoisomers" as used herein refer to stereoisomers that are not mirror images of each other and are non-superimposable. Similarly, the term "enantiomers" as used herein refer to stereoisomers that are mirror images of each other, but are non-superimposable. Thus, the relevant asymmetric center is described by the R- and S-sequencing rules of Cahn and Prelog. A chiral compound can exist as a single enantiomer or mixture thereof, i.e., a "racemic mixture." The asymmetric center may also be described by the manner in which the molecule rotates the plane of polarized light and designated as dextrorotatory (+) or levorotatory (−).

In other aspects, the compound of formula (VIII) may be selected from among:

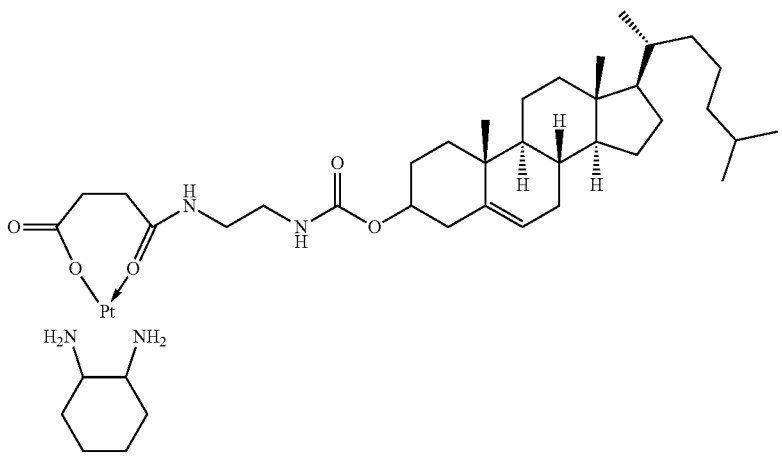

$C_{40}H_{69}N_4O_5Pt$
Mol. Wt.: 881.08

17
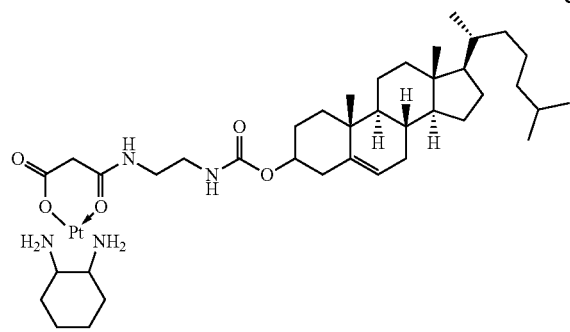
C₃₉H₆₇N₄O₅Pt
Mol. Wt.: 867.05
18
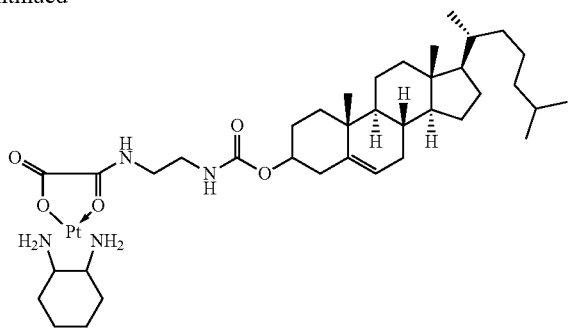
C₃₈H₆₅N₄O₅Pt
Mol. Wt.: 853.02
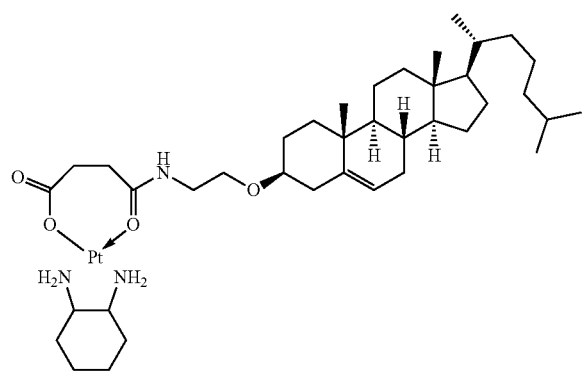
C₃₉H₆₈N₃O₄Pt
Mol. Wt.: 838.05
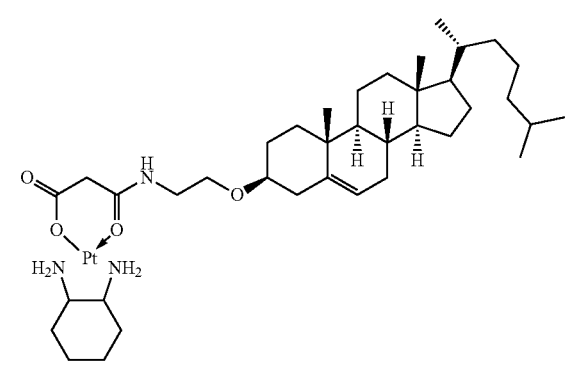
C₃₈H₆₆N₃O₄Pt
Mol. Wt.: 824.03
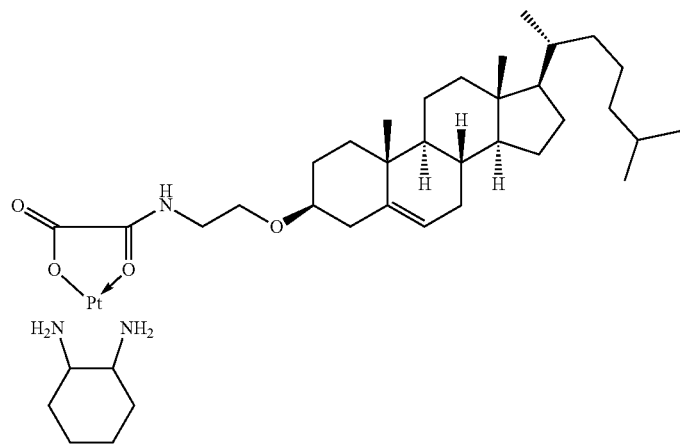
C₃₇H₆₄N₃O₄Pt
Mol. Wt.: 810.00

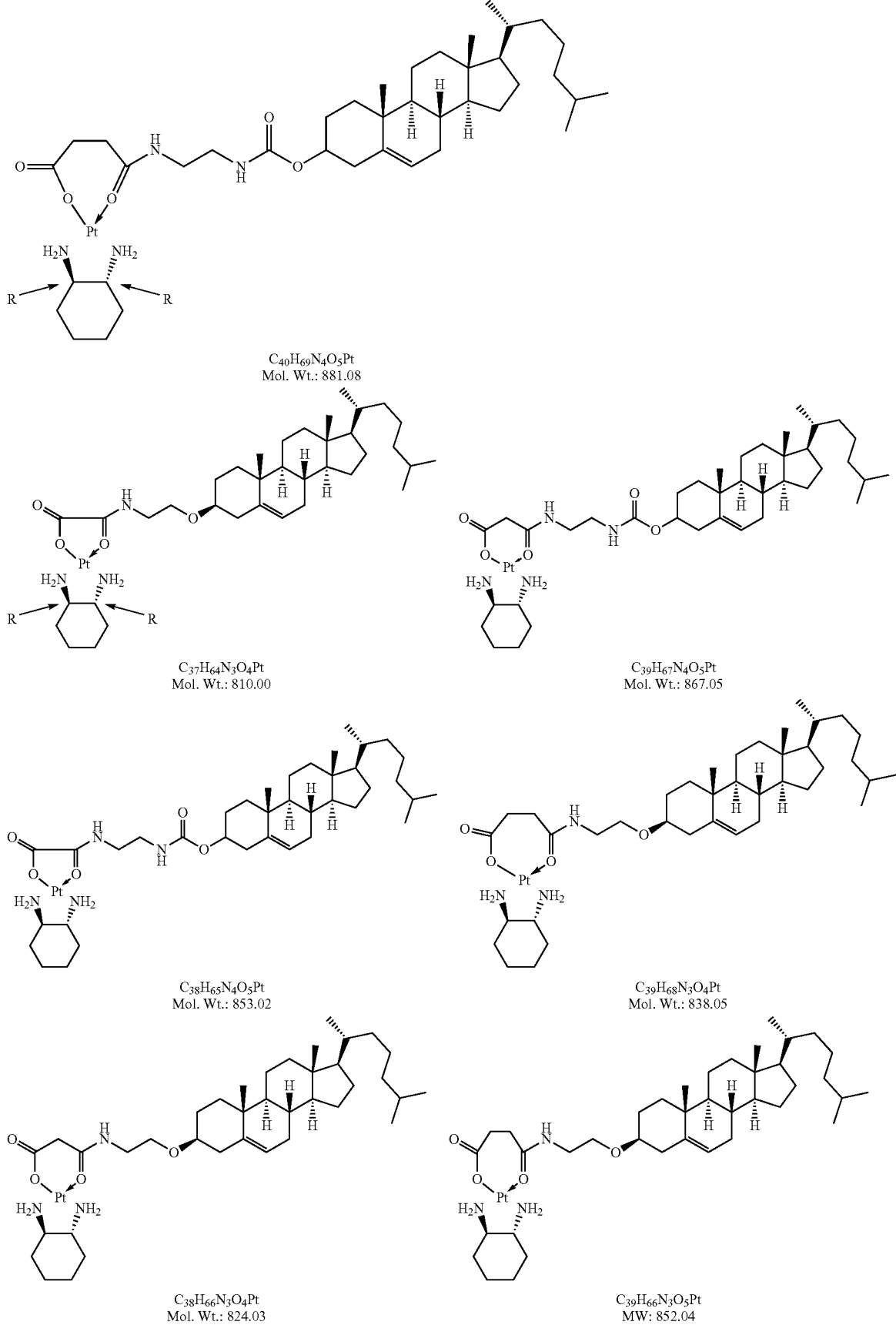

-continued
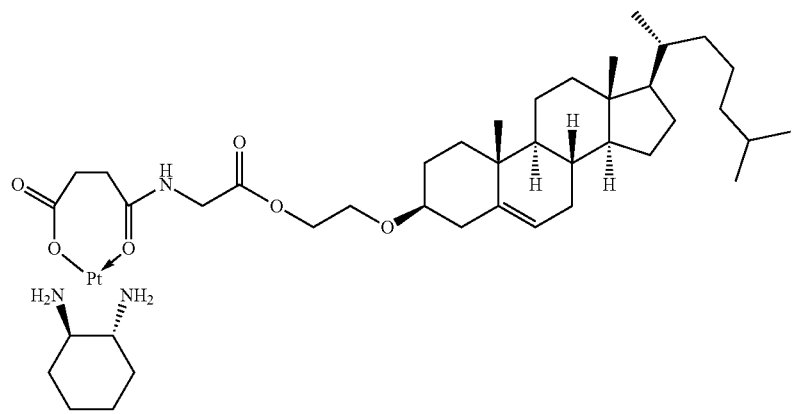
C₄₁H₇₀N₃O₆Pt
MW: 896.09
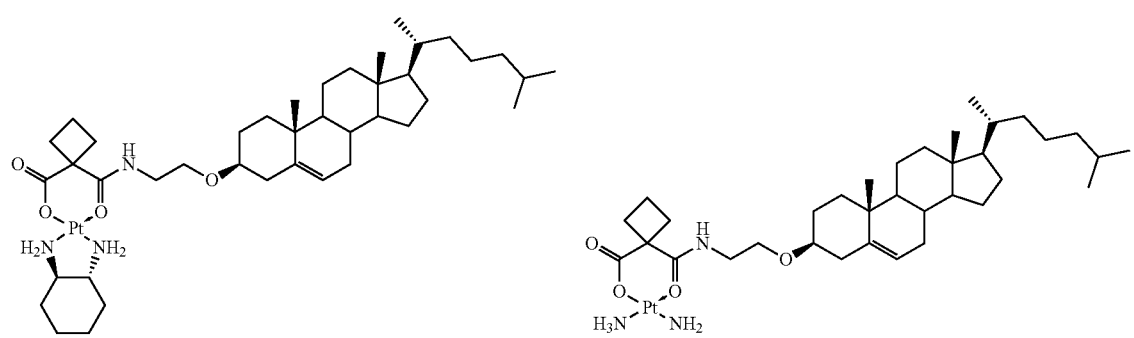
C₄₁H₆₈N₃O₄Pt
MW: 862.07
C₃₅H₆₂N₃O₄Pt
MW: 783.96
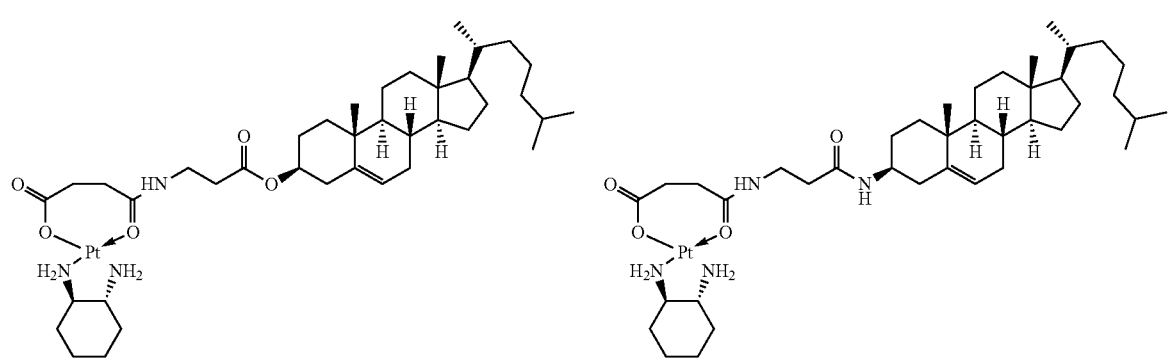
C₄₀H₆₈N₃O₅Pt
MW: 866.06
C₄₀H₆₉N₄O₄Pt
MW: 865.08

-continued
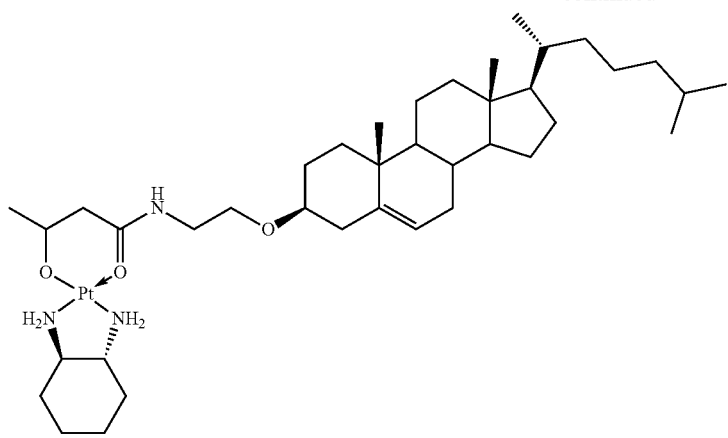
C<sub>39</sub>H<sub>68</sub>N<sub>3</sub>O<sub>3</sub>Pt
MW: 822.05
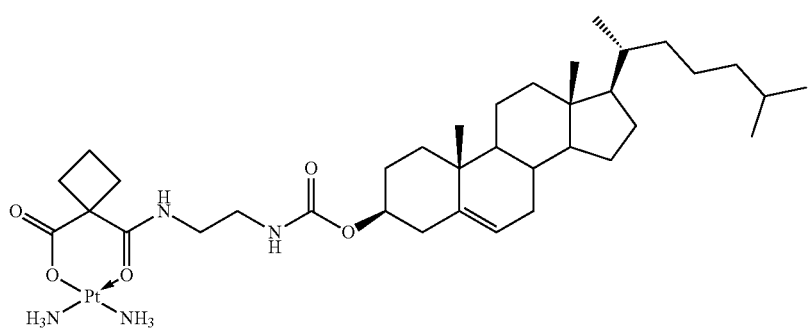
C<sub>36</sub>H<sub>63</sub>N<sub>4</sub>O<sub>5</sub>Pt
MW: 826.99
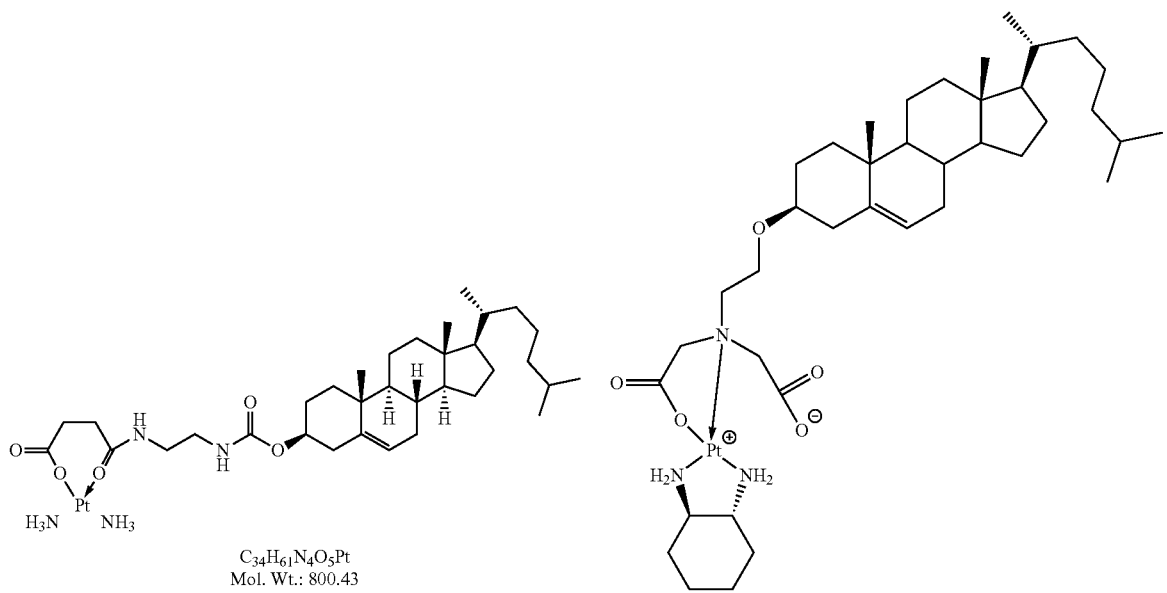
C<sub>34</sub>H<sub>61</sub>N<sub>4</sub>O<sub>5</sub>Pt
Mol. Wt.: 800.43

25
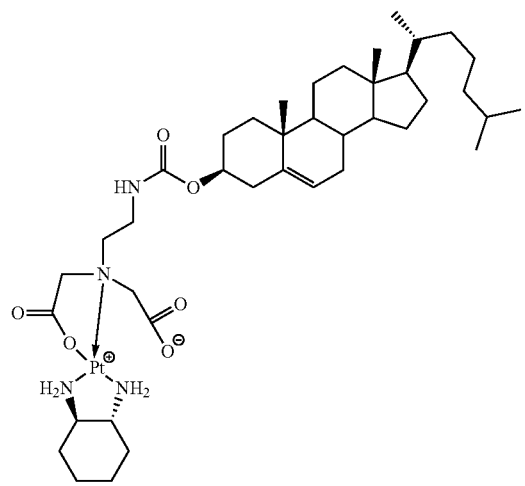
26
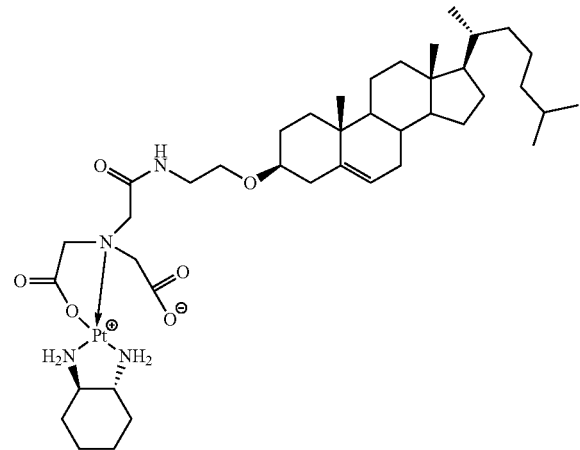
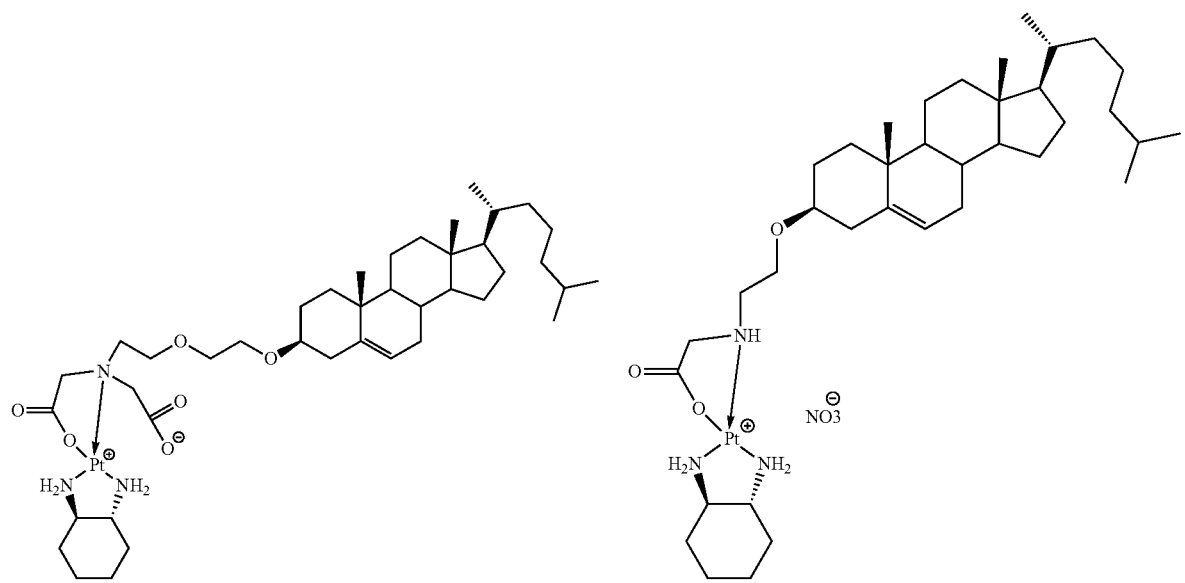
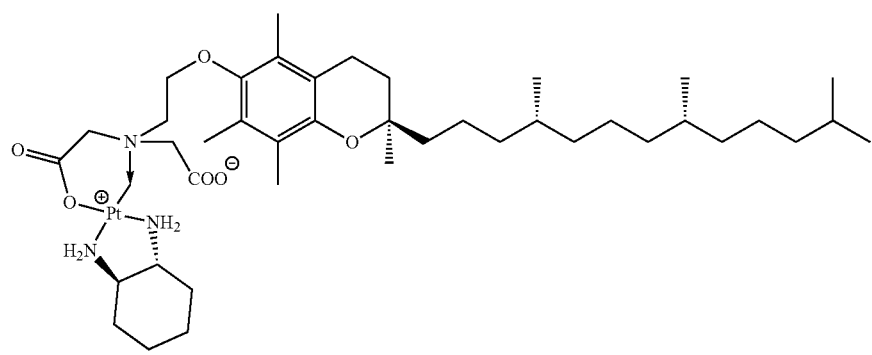
Lipid = alpha tocopherol -continued
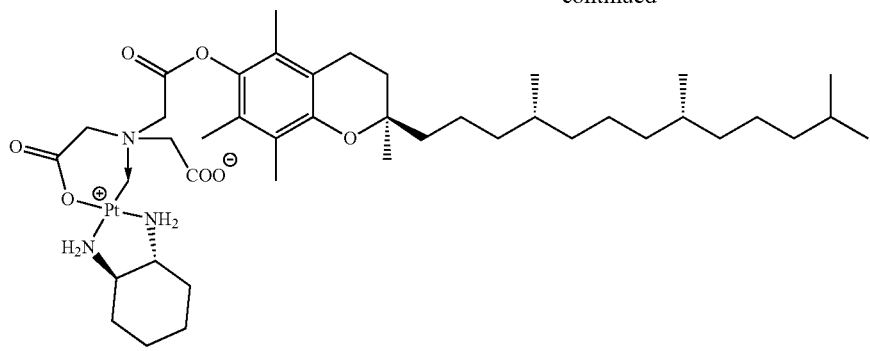
Lipid = alpha tocopherol
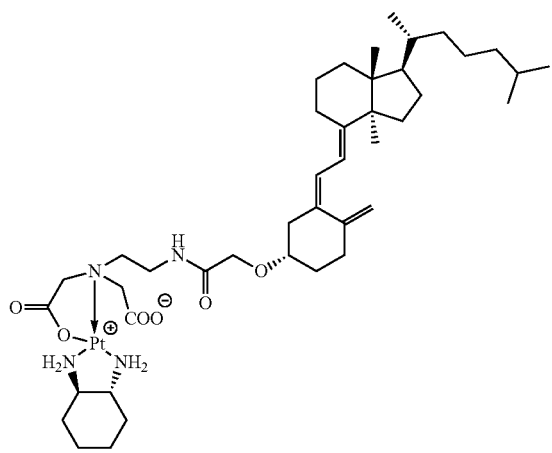
lipid = vitamine D3
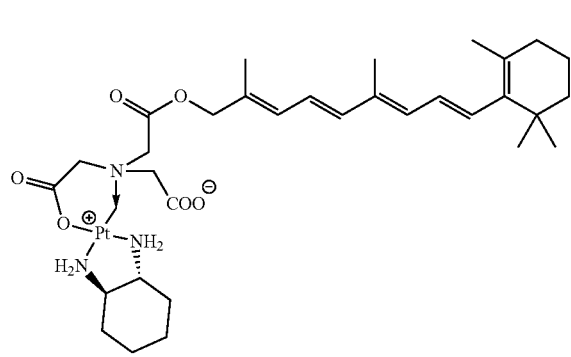
Lipid = vitamin A
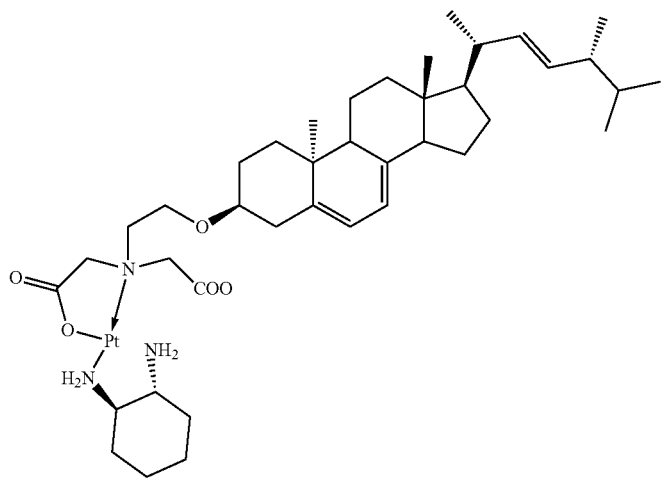
Lipid = Lumisterol
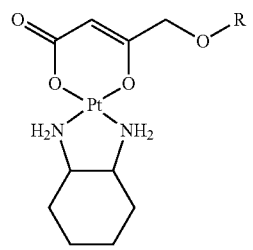
R = Lipid, Aromatic
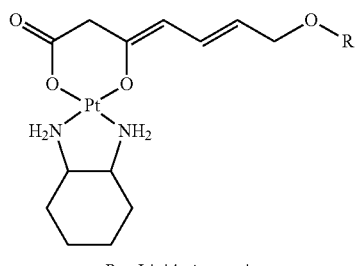
R = Lipid, Aromatic
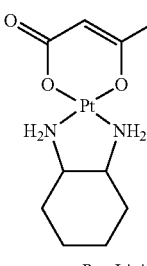
R = Lipid, Aromatic
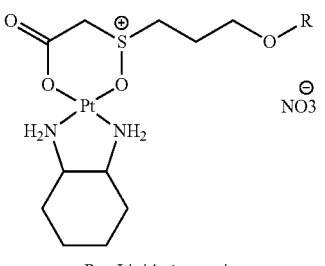
R = Lipid, Aromatic 29
-continued
30
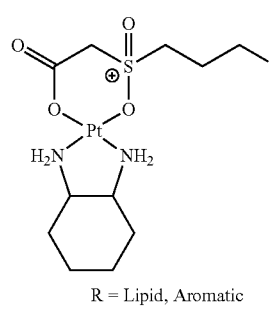
R = Lipid, Aromatic
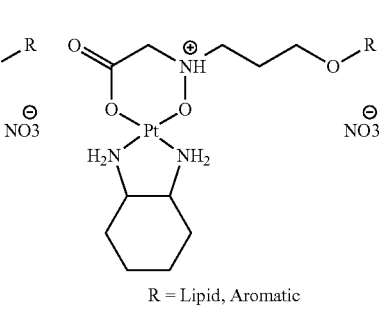
R = Lipid, Aromatic
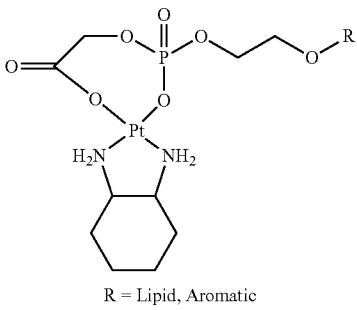
R = Lipid, Aromatic
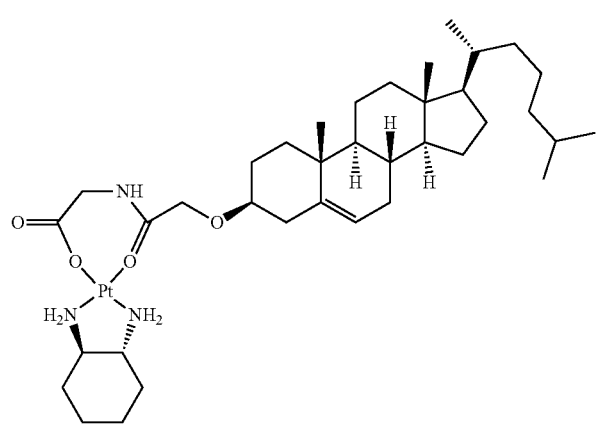
$C_{38}H_{66}N_3O_3Pt$
Mol. Wt.: 810.00
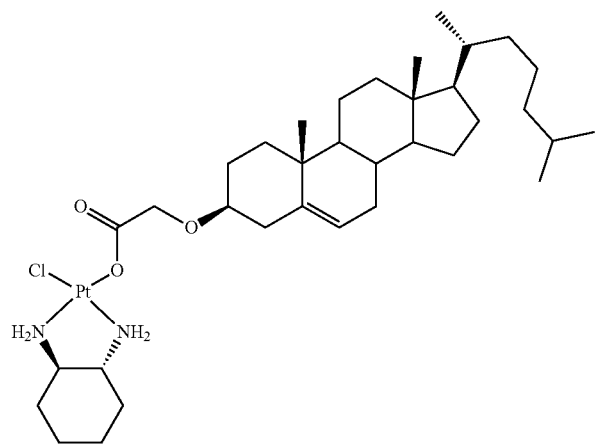
$C_{39}H_{65}N_3O_6Pt$
MW = 867.03
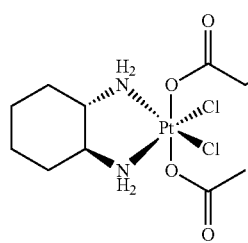
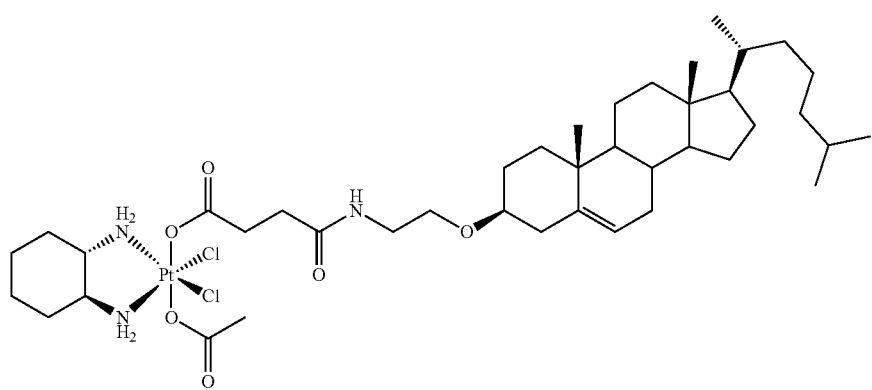

-continued
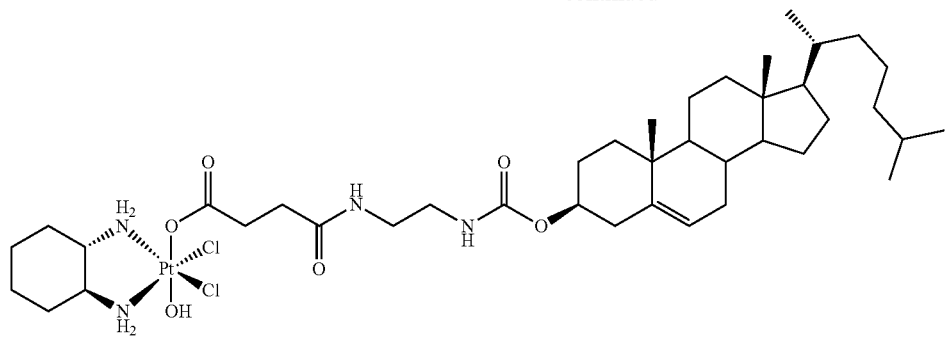
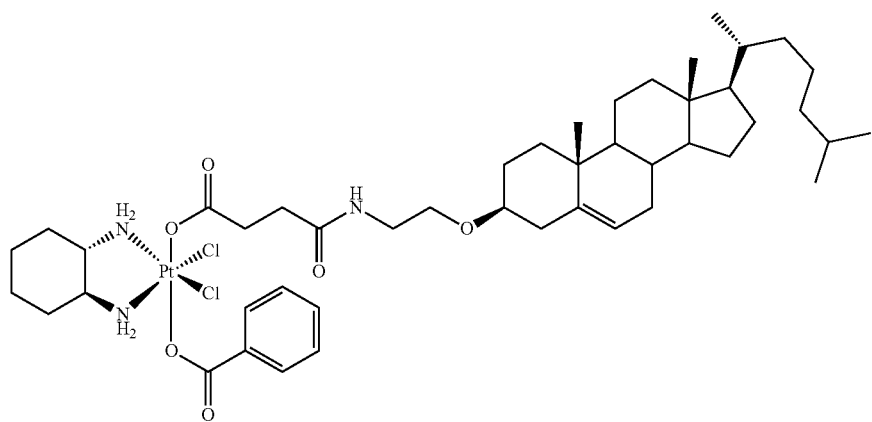
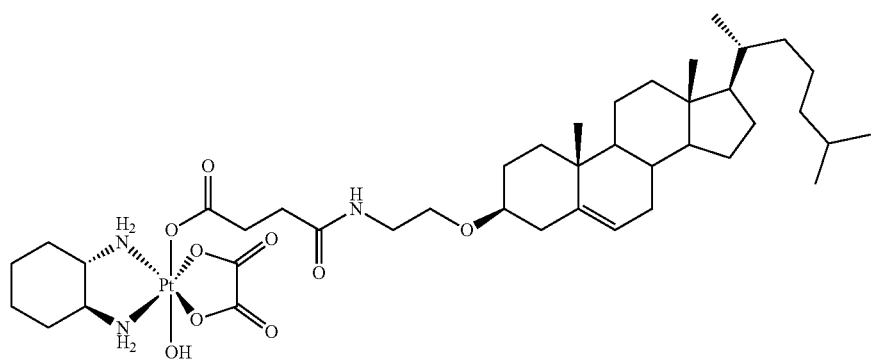
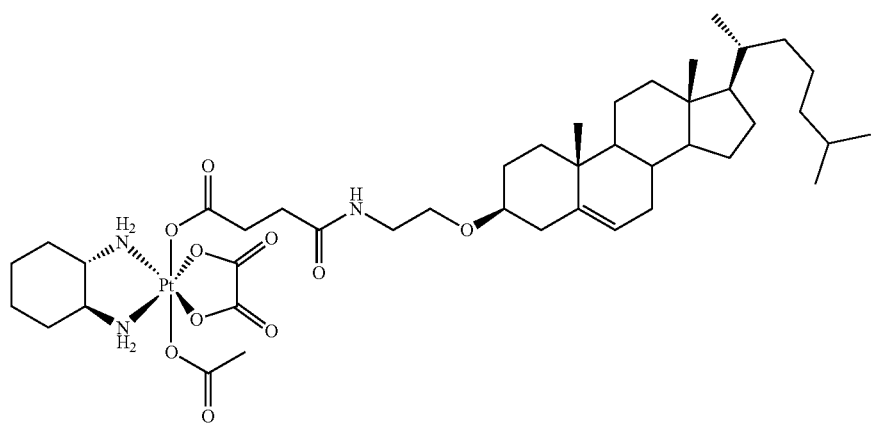

33
34
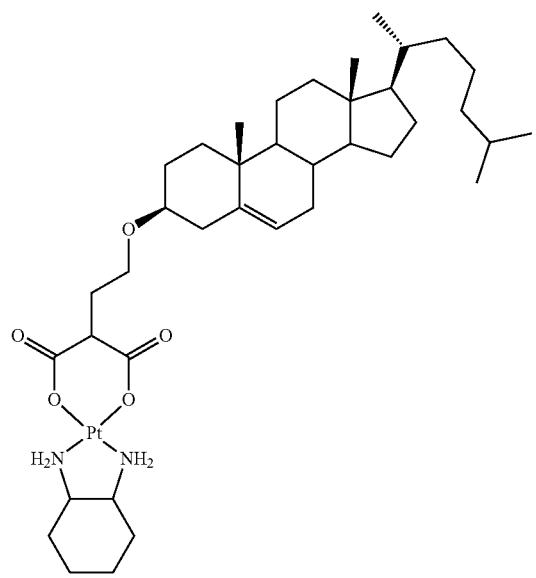
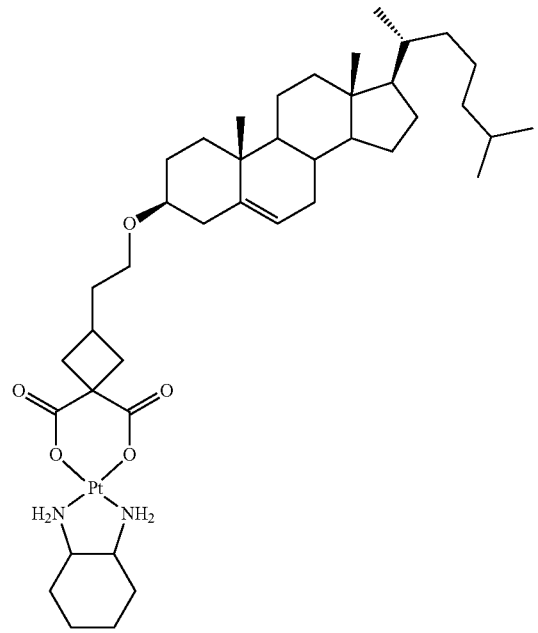
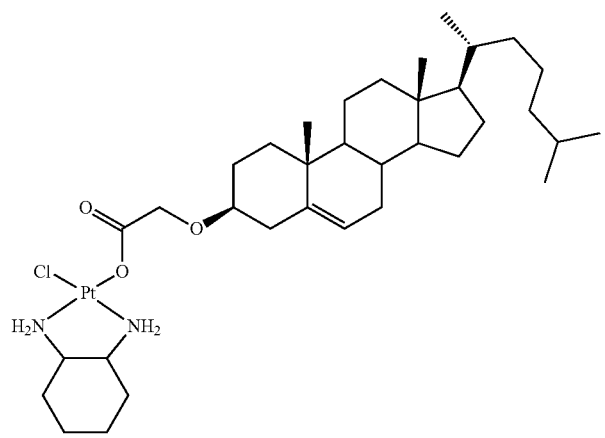
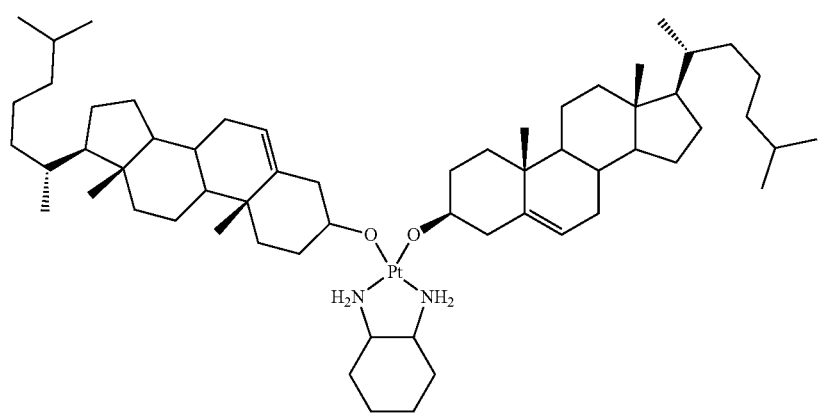

-continued
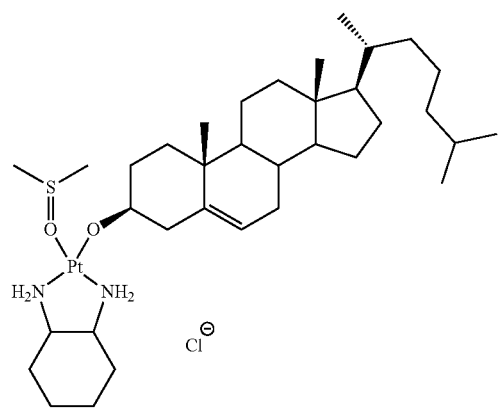
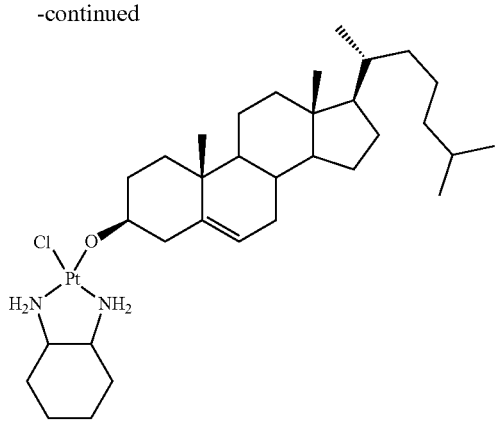
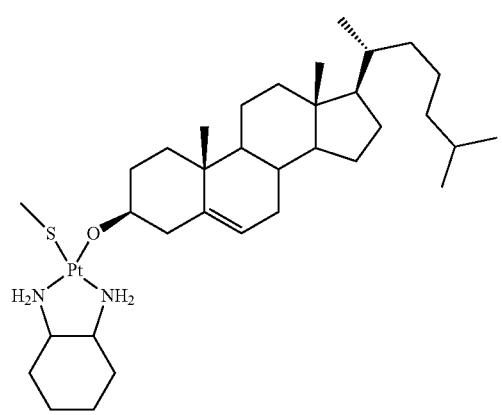
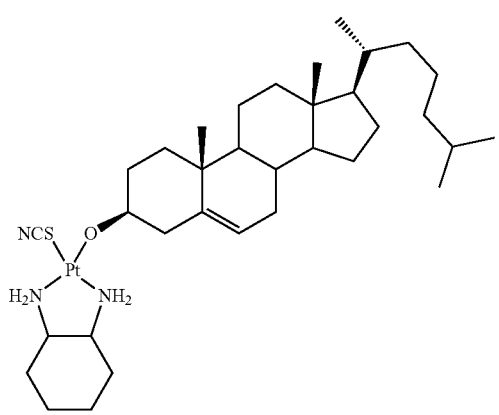
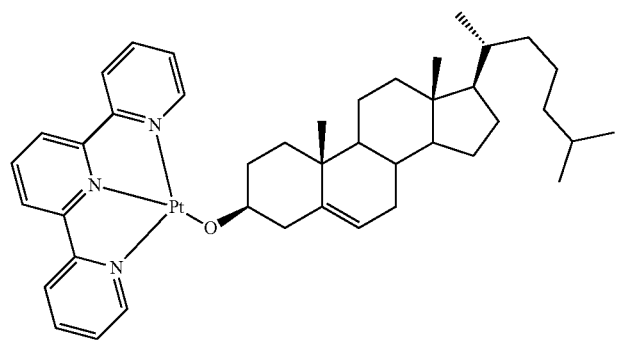
These compounds, including the compounds of formula (VIII) and IO-125, may be prepared as described in U.S. Patent Application Publication No. 2016/0145284, which is incorporated by reference herein.
The compounds described herein may contain asymmetric centers. In some embodiments, IO-125 refers to a compound having the following structure:

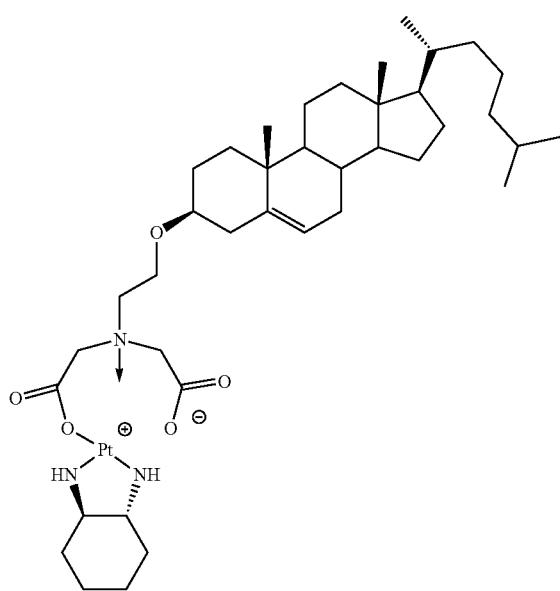

"Pharmaceutically acceptable salt" as used herein refers to salts of the compounds of formula (VIII), such as IO-125, that are pharmaceutically acceptable and possess the activity of the neutral compound of formula (VIII), such as IO-125. The salts are non-toxic and include inorganic acid, organic acid, or base addition salts. In some embodiments, the salts are inorganic acid salts. In other embodiments, the salts are formed with inorganic acids including, without limitation, hydrochloric acid, hydrobromic acid, sulfuric acid, nitric acid, or phosphoric acid. In further embodiments, the salts are formed using organic acids. In still other embodiments, the salts are formed with organic acids including, without limitation, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, or muconic acid. The pharmaceutically acceptable salts may also formed by replacing an acidic proton in the compounds of formula (VIII), such as IO-125, with metal ion (alkali, alkaline earth, aluminum) or coordinates with an organic base (ethanolamine, diethanolamine, triethanolamine, N-methylglucamine).

The terms "subject" and "patient" are used interchangeably and include, without limitation, mammals. In some embodiments, the patient or subject is a human. In other embodiments, the patient or subject is a veterinary or farm animal, a domestic animal or pet, or animal used for clinical research.

"Treating" or variations thereof refers ameliorating or reducing the development of a disease or disorder, i.e., delaying the onset of the disease. In other embodiments, "treating" refers to ameliorating or reducing at least one physical parameter of the disease or disorder.

The disease or disorder that may be treated with the compounds of formula (VIII), such as IO-125, and an immune checkpoint inhibitor is cancer. In some embodiments, the cancer stifles activation of the patient's cells that attack cancer cells. In other embodiments, the cancer stifle's activation of the patients B-cells, T-cells, monocytes, macrophages, natural killer cells, dendritic cells or a combination thereof. Thus, by activating the response by the B-cells, T-cells, monocytes, macrophages, natural killer cells, dendritic cells or a combination thereof, the methods discussed herein result in reduced occurrences of relapse, i.e., reduced reoccurrences of cancer.

In some embodiments, the cancer is prostate cancer, colorectal cancer, pancreatic cancer, cervical cancer, stomach cancer, endometrial cancer, brain cancer, liver cancer, bladder cancer, ovarian cancer, testicle cancer, head cancer, neck cancer, skin cancer such as melanoma or basal carcinoma, mesothelial lining cancer, white blood cell cancer such as lymphoma or leukaemia, esophageal cancer, breast cancer, muscle cancer, connective tissue cancer, lung cancer such as small-cell lung carcinoma or non-small-cell carcinoma, adrenal gland cancer, thyroid cancer, kidney cancer, or bone cancer. In other embodiments, the cancer is prostate cancer. In further embodiments, the cancer is colorectal cancer. In other embodiments, the cancer is pancreatic cancer. In still further embodiments, the cancer is cervical cancer. In further embodiments, the cancer is stomach cancer. In other embodiments, the cancer is endometrial cancer. In yet further embodiments, the cancer is brain cancer. In still other embodiments, the cancer is liver cancer. In further embodiments, the cancer is bladder cancer.

In other embodiments, the cancer is ovarian cancer. In still further embodiments, the cancer is testicle cancer. In yet other embodiments, the cancer is head cancer. In further embodiments, the cancer is neck cancer. In other embodiments, the cancer is skin cancer. In yet further embodiments, the cancer is skin cancer such as melanoma or basal carcinoma. In still other embodiments, the cancer is mesothelial lining cancer. In further embodiments, the cancer is a white blood cell cancer. In other embodiments, the cancer is a white blood cell cancer such as lymphoma or leukaemia. In yet further embodiments, the cancer is esophageal cancer. In still other embodiments, the cancer is breast cancer. In other embodiments, the cancer is triple negative breast cancer (TNBC) or luminal B-type breast cancer. In further embodiments, the cancer is muscle cancer. In other embodiments, the cancer is connective tissue cancer. In yet further embodiments, the cancer is lung cancer. In still other embodiments, the cancer is lung cancer such as small-cell lung carcinoma or non-small-cell carcinoma. In further embodiments, the cancer is adrenal gland cancer. In other embodiments, the cancer is thyroid cancer. In still further embodiments, the cancer is kidney cancer. In yet other embodiments, the cancer is bone cancer.

As described, a therapeutically effective amount of the compounds of formula (VIII), such as IO-125, or a pharmaceutically acceptable salt thereof, and a therapeutically effective amount of an immune checkpoint inhibitor are administered to a patient. In some embodiments, the compounds of formula (VIII) and immune checkpoint inhibitor are administered separately. In further embodiments, the IO-125 and immune checkpoint inhibitor are administered separately. In other embodiments, the compounds of formula (VIII) and immune checkpoint inhibitor are administered simultaneously. In yet further embodiments, the IO-125 and immune checkpoint inhibitor are administered simultaneously. When administered simultaneously, the the compounds of formula (VIII), such as IO-125, may be formulated together. For example, the compound of formula (VIII) and an immune checkpoint inhibitor may be present in a single pharmaceutical formulation or may be formulated in separate pharmaceutical formulations. In another example, IO-125 and an immune checkpoint inhibitor may be present in a single pharmaceutical formulation or may be formulated in separate pharmaceutical formulations.

Also described are methods for enhancing the immune response of a subject suffering from cancer and comprise administering to the patient a therapeutically effective amount of IO-125, or a pharmaceutically acceptable salt thereof, and a therapeutically effective amount of an immune checkpoint inhibitor or methods for enhancing the immune response of a subject suffering from cancer and comprise administering to the patient a therapeutically effective amount of a compound of formula (VIII), or a pharmaceutically acceptable salt thereof, and a therapeutically effective amount of an immune checkpoint inhibitor. The term "enhancing the immune response" of a subject refers to the activation or re-activation of the subject's cells, e.g., B-cells, T-cells, monocytes, macrophages, natural killer cells, dendritic cells or a combination thereof, to attack the cancer cells.

Further provided are methods for preventing metastasis or relapse of a cancer in a subject and comprise administering to the patient a therapeutically effective amount of IO-125, or a pharmaceutically acceptable salt thereof, and a therapeutically effective amount of an immune checkpoint inhibitor or methods for preventing metastasis or relapse of a cancer in a subject and comprise administering to the patient a therapeutically effective amount of a compound of formula (VIII), or a pharmaceutically acceptable salt thereof, and a therapeutically effective amount of an immune checkpoint inhibitor. The term "metastasis" as used herein refers to the spread of a cancer beyond its original origin. The term relapsed" as used herein refers to the re-emergence of a cancer in a patient who has not had symptoms of cancer for at least about 1 year, about 2 years, about 3 years, about 4 years, about 5 years or more.

A therapeutically effective amount of the compound of formula (VIII), such as IO-125, or salt thereof is administered to a subject suffering from or diagnosed as having cancer. As used herein, a "therapeutically effective amount" refers to an amount or dose sufficient to reduce or ameliorate cancer cells in a patient. Therapeutically effective amounts may be determined by those skilled in the art, such as an attending physician, using modeling, dose escalation studies or clinical trials. In some embodiments, the therapeutically effective amount of the compound of formula (VIII), such as IO-125, is in the range of from about 0.001 to about 200 mg of compound per kg of subject's body weight per day. In other embodiments, the therapeutically effective amount is about 0.05 to about 100 mg/kg/day. In further embodiments, the therapeutically effective amount is about 1 to about 35 mg/kg/day. In yet other embodiments, the therapeutically effective amount is about 1 to about 30, about 1 to about 25, about 1 to about 20, about 1 to about 15, about 1 to about 10, about 1 to about 5, about 5 to about 35, about 5 to about 30, about 5 to about 25, about 5 to about 20, about 5 to about 15, about 5 to about 10, about 10 to about 35, about 10 to about 30, about 10 to about 25, about 10 to about 20, about 10 to about 15, about 15 to about 35, about 15 to about 30, about 15 to about 25, about 15 to about 20, about 20 to about 35, about 20 to about 30, or about 25 to about 35 mg/kg/day. By way of example, a 70-kg human, an illustrative range for a dose of the compound of formula (VIII), such as IO-125, or salt thereof is from about 0.001 to about 7, about 0.1 to about 7, about 0.5 to about 7, about 1 to about 7, about 2 to about 7, about 3 to about 7, about 4 to about 7, about 5 to about 7, about 0.1 to about 5, about 0.1 to about 4, about 0.1 to about 3, about 0.1 to about 2, about 0.2 to about 7, about 0.2 to about 6, about 0.2 to about 5, about 0.2 to about 4, about 0.2 to about 3, or about 0.2 to about 2.5 g/day.

Alternatively, the therapeutically effective amount is about 0.001 to about 500 mg/kg/day. In yet other embodiments, the therapeutically effective amount is about 0.001 to about 400, about 0.001 to about 300, about 0.001 to about 200, about 0.005 to about 400, about 0.005 to about 300, about 0.005 to about 200, about 0.010 to about 400, about 0.010 to about 300, about 0.010 to about 200, about 0.05 to about 400, about 0.05 to about 300, about 0.05 to about 200, about 0.1 to about 400, about 0.1 to about 300, about 0.1 to about 200, about 0.5 to about 400, about 0.5 to about 300, or about 0.5 to about 200 mg/kg/day. By way of example, a 70-kg human, an illustrative range for a dose of the compound of formula (VIII), such as IO-125, or salt thereof is from about 0.00007 to about 28, about 0.00007 to about 21, about 0.00007 to about 14, about 0.00035 to about 28, about 0.00035 to about 21, about 0.00035 to about 14, about 0.0007 to about 28, about 0.0007 to about 21, about 0.0007 to about 14, about 0.0035 to about 28, about 0.0035 to about 21, about 0.0035 to about 14, about 0.007 to about 28, about 0.007 to about 21, about 0.007 to about 14, about 0.035 to about 28, about 0.035 to about 21, or about 0.035 to about 14 g/day.

The therapeutically effective amount may be administered in single or divided dosage units. As used herein, the term "immune checkpoint inhibitor" refers to a chemical moiety that blocks the activity of molecules involved in attenuating the immune response. In some embodiments, the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

In some aspects, the immune checkpoint inhibitor is an A2AR inhibitor.

In other aspects, the immune checkpoint inhibitor is an arginase inhibitor.

In further aspects, the immune checkpoint inhibitor is a B7-H3 inhibitor.

In yet other aspects, the immune checkpoint inhibitor is a B7-H4 inhibitor.

In still further aspects, the immune checkpoint inhibitor is a BTLA inhibitor.

In other aspects, the immune checkpoint inhibitor is a CD47 inhibitor.

In further aspects, the immune checkpoint inhibitor is a CD73 inhibitor.

In still other aspects, the immune checkpoint inhibitor is a CD96 inhibitor.

In yet further aspects, the immune checkpoint inhibitor is a CSF1R inhibitor.

In other aspects, the immune checkpoint inhibitor is a CTLA-4 inhibitor. In some embodiments, the immune checkpoint inhibitor is a CTLA-4 inhibitor that is an anti-CTLA-4 antibody. In other embodiments, the immune checkpoint inhibitor is an anti-CTLA-4 antibody that is ipilimumab.

In further aspects, the immune checkpoint inhibitor is a JAK inhibitor. In some embodiments, the immune checkpoint inhibitor is a JAK immune inhibitor that is a JAK1 inhibitor, JAK2 inhibitor, or a combination thereof. In other embodiments, the immune checkpoint inhibitor is a JAK1 inhibitor. In further embodiments, the immune checkpoint inhibitor is a JAK2 inhibitor.

In yet other aspects, the immune checkpoint inhibitor is a LAG3 inhibitor. In some embodiments, the immune checkpoint inhibitor is a LAG inhibitor that is an anti-LAG3 antibody. In other embodiments, the immune checkpoint inhibitor is an anti-LAG3 antibody that is BMS-986016 or LAG525. In further embodiments, the immune checkpoint inhibitor is BMS-986016 or LAG525. In yet other embodiments, the immune checkpoint inhibitor is LAG525.

In still further aspects, the immune checkpoint inhibitor is a PI3K delta inhibitor.

In other aspects, the immune checkpoint inhibitor is a PI3K gamma inhibitor.

In yet other aspects, the immune checkpoint inhibitor is a PD-1 inhibitor. In some embodiments, the immune checkpoint inhibitor is a PD-1 inhibitor that is an anti-PD-1 monoclonal antibody. In further embodiments, the immune checkpoint inhibitor is an anti-PD-1 monoclonal antibody that is nivolumab, pembrolizumab, pidilizumab, SHR-1210, PDR001, or AMP-224. In other embodiments, the immune checkpoint inhibitor is an anti-PD-1 monoclonal antibody that is nivolumab or pembrolizumab. In yet further embodiments, the immune checkpoint inhibitor is nivolumab. In still other embodiments, the immune checkpoint inhibitor is pembrolizumab. In further embodiments, the immune checkpoint inhibitor is pidilizumab. In other embodiments, the immune checkpoint inhibitor is SHR-1210. In still further embodiments, the immune checkpoint inhibitor is PDR001. In other embodiments, the immune checkpoint inhibitor is AMP-224.

In still further aspects, the immune checkpoint inhibitor is a PD-L1 inhibitor. In some embodiments, the immune checkpoint inhibitor is a PD-L1 inhibitor that is an anti-PD-L1 monoclonal antibody. In other embodiments, the immune checkpoint inhibitor is an anti-PD-L1 monoclonal antibody that is atezolizumab, avelumab, durvalumab, BMS-935559, MEDI4736, MPDL3280A, or MSB0010718C. In further embodiments, the immune checkpoint inhibitor is atezolizumab. In yet other embodiments, the immune checkpoint inhibitor is avelumab. In still further embodiments, the immune checkpoint inhibitor is durvalumab. In other embodiments, the immune checkpoint inhibitor is BMS-935559. In further embodiments, the immune checkpoint inhibitor is MEDI4736. In yet other embodiments, the immune checkpoint inhibitor is MPDL3280A. In still further embodiments, the immune checkpoint inhibitor is MSB0010718C.

In other aspects, the immune checkpoint inhibitor is a PD-L2 inhibitor.

In further aspects, the immune checkpoint inhibitor is a TAM inhibitor.

In still other aspects, the immune checkpoint inhibitor is TIM3 inhibitor. In some embodiments, the immune checkpoint inhibitor is a TIM3 inhibitor that is an anti-TIM3 antibody.

In yet further aspects, the immune checkpoint inhibitor is a VISTA inhibitor.

In other aspects, the immune checkpoint inhibitor is a stimulatory checkpoint inhibitor. In some embodiments, the immune checkpoint inhibitor is a stimulatory checkpoint molecule that is CD27, CD28, CD40, CD122, an inducible T-cell costimulator (ICOS), OX40, glucocorticoid induced TNF receptor (GITR), or CD137. In other embodiments, the immune checkpoint inhibitor is a CD27 stimulatory checkpoint molecule. In further embodiments, the immune checkpoint inhibitor is a CD28 stimulatory checkpoint molecule. In still other embodiments, the immune checkpoint inhibitor is a CD40 stimulatory checkpoint molecule. In yet further embodiments, the immune checkpoint inhibitor is a CD122 stimulatory checkpoint molecule. In other embodiments, the immune checkpoint inhibitor is ICOS checkpoint molecule. In further embodiments, the immune checkpoint inhibitor is an OX40 stimulatory checkpoint molecule. In yet other embodiments, the immune checkpoint inhibitor is a GITR stimulatory checkpoint molecule. In still further embodiments, the immune checkpoint inhibitor is a CD137 stimulatory checkpoint molecule. In yet other aspects, the immune checkpoint inhibitor is a GITR inhibitor. In some embodiments, the immune checkpoint inhibitor is a GITR inhibitor that is an anti-GITR antibody. In other embodiments, the immune checkpoint inhibitor that is an anti-GITR antibody that is TRX518, MK-4166, or INCAGN01876. In further embodiments, the immune checkpoint inhibitor is TRX518. In yet other embodiments, the immune checkpoint inhibitor is MK-4166. In still further embodiments, the immune checkpoint inhibitor is INCAGN01876. In still further aspects, the immune checkpoint inhibitor is an OX40 inhibitor. In some embodiments, the immune checkpoint inhibitor is an anti-OX40 antibody. In other embodiments, the immune checkpoint inhibitor is an OX40L fusion protein. In further embodiments, the immune checkpoint inhibitor is an anti-OX40 antibody that is MED10562 or INCAGN01949. In yet other embodiments, the immune checkpoint inhibitor is MED10562. In still further embodiments, the immune checkpoint inhibitor is INCAGN01949. In other embodiments, the immune checkpoint inhibitor is an OX40L fusion protein that is MED16383.

A therapeutically effective amount of the immune checkpoint inhibitor may be determined by those skilled in the art, such as an attending physician, using modeling, dose escalation studies or clinical trials. In some embodiments, the therapeutically effective amount of the immune checkpoint inhibitor is in the range of from about 0.001 to about 200 mg of compound per kg of subject's body weight per day. In other embodiments, the therapeutically effective amount is about 0.05 to about 100 mg/kg/day. In further embodiments, the therapeutically effective amount of the immune checkpoint inhibitor is about 1 to about 35 mg/kg/day. In yet other embodiments, the therapeutically effective amount of the immune checkpoint inhibitor is about 1 to about 30, about 1 to about 25, about 1 to about 20, about 1 to about 15, about 1 to about 10, about 1 to about 5, about 5 to about 35, about 5 to about 30, about 5 to about 25, about 5 to about 20, about 5 to about 15, about 5 to about 10, about 10 to about 35, about 10 to about 30, about 10 to about 25, about 10 to about 20, about 10 to about 15, about 15 to about 35, about 15 to about 30, about 15 to about 25, about 15 to about 20, about 20 to about 35, about 20 to about 30, or about 25 to about 35 mg/kg/day. By way of example, a 70-kg human, an illustrative range for a dose of the immune checkpoint inhibitor is from about 0.001 to about 7, about 0.1 to about 7, about 0.5 to about 7, about 1 to about 7, about 2 to about 7, about 3 to about 7, about 4 to about 7, about 5 to about 7, about 0.1 to about 5, about 0.1 to about 4, about 0.1 to about 3, about 0.1 to about 2, about 0.2 to about 7, about 0.2 to about 6, about 0.2 to about 5, about 0.2 to about 4, about 0.2 to about 3, or about 0.2 to about 2.5 g/day. The therapeutically effective amount of the immune checkpoint inhibitor may be administered in single or divided dosage units.

Additional active ingredients may also be utilized in the methods and pharmaceutical compositions described herein.

In some embodiments, the additional active ingredient is a killer-cell immunoglobulin-like receptors (KIR) inhibitor, T cell immunoreceptor with Ig and ITIM domains (TIGIT) inhibitor, leukocyte-associated immunoglobulin-like receptor 1 (LAIR1) inhibitor, CD160 inhibitor, 2B4 inhibitor, transforming growth factor receptor (TGFR) beta inhibitor, or a combination thereof. In other embodiments, the additional active ingredient is a KIR inhibitor. In further embodiments, the additional active ingredient is a TIGIT inhibitor. In yet other embodiments, the additional active ingredient is a LAIR1 inhibitor. In still further embodiments, the additional active ingredient is a CD160 inhibitor. In other embodiments, the additional active ingredient is a 2B4 inhibitor. In further embodiments, the additional active ingredient is a TGFR beta inhibitor. Other additional active ingredients include, without limitation, toll-like receptor (TLR) agonists, lymphocyte-specific protein tyrosine kinase (LCK) activators, natural killer (NK) cell activators, or granulocyte-macrophage colony-stimulating factor (GM-CSF). These active ingredients may be formulated with one or both of the compound of formula (VIII) IO—125 or immune checkpoint inhibitor or may be separately administered to the patient as determined by one skilled in the art. These active ingredients also may be formulated with one or both of the IO-125 or immune checkpoint inhibitor or may be separately administered to the patient as determined by one skilled in the art.

Thus, the present disclosure also provides pharmaceutical compositions comprising a compound of formula (VIII), or a pharmaceutically acceptable salt thereof, an immune checkpoint inhibitor, and a pharmaceutically acceptable excipient or pharmaceutical compositions comprising IO-125, or a pharmaceutically acceptable salt thereof, an immune checkpoint inhibitor, and a pharmaceutically acceptable excipient.

The pharmaceutical formulations described herein may be administered by any suitable means including, without limitation, oral, rectal, nasal, parenteral (i.e., subcutaneous, intradermal, intramuscular, intraperitoneal, intravenous, intraarticular, intramedullar), intraperitoneal, transmucosal, transdermal, or topical (i.e., dermal, buccal, sublingual, intraocular). The pharmaceutical formulations are tailored to the particular administration route.

Thus, in some embodiments, the pharmaceutical formulations are in the form of tablets, capsules (hard and soft gelatin capsules), sachets, dragees, powders, granules, lozenges, powders for reconstitution, liquid preparations (solutions, emulsions, suspensions, or syrups), patches, inhalants, or suppositories.

The pharmaceutically acceptable excipients are selected based on the mode of administration and may include inert and/or active components. In some embodiments, the pharmaceutically acceptable excipient is sterile, non-toxic, and/or biologically suitable for administration to a subject, i.e., buffered to an appropriate pH and isotonicity. In other embodiments, the pharmaceutically acceptable excipients include diluents (such as inert), carrier, adjuvant, fillers, disintegrants, binders, lubricants, sweeteners, flavors, colors, or preservatives.

ASPECTS

Aspect 1. A method for treating cancer in a patient, comprising administering to the patient:
(i) a therapeutically effective amount of a compound of the following structure, or a pharmaceutically acceptable salt thereof;

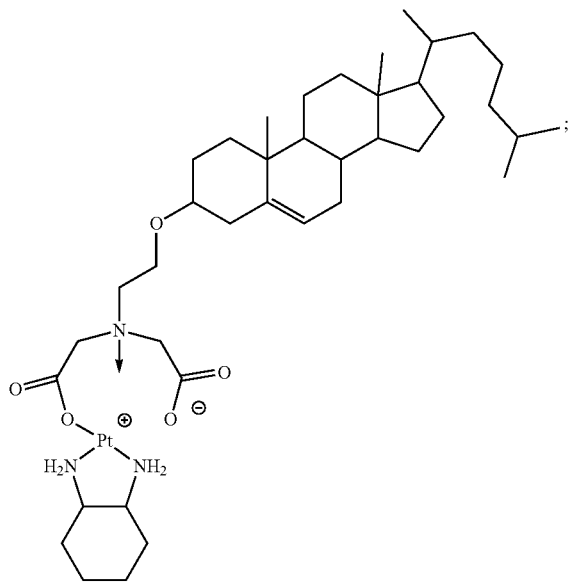

and
(ii) a therapeutically effective amount of an immune checkpoint inhibitor.

Aspect 2. The method of aspect 1, wherein the immune checkpoint inhibitor is an inhibitor against A2AR, arginase, B7-H3, B7-H4, BTLA, CD47, CD73, CD96, CSF1R, CTLA-4, JAK, LAG3, PI3K delta, PI3K gamma, PD-1, PD-L1, PD-L2, TAM, TIM3, VISTA, a stimulatory checkpoint molecule, or a combination thereof.

Aspect 3. The method of aspect 2, wherein the JAK immune checkpoint inhibitor is a JAKI inhibitor, JAK2 inhibitor, or a combination thereof.

Aspect 4. The method of aspect 2, wherein the stimulatory checkpoint molecule is CD27, CD28, CD40, CD122, ICOS, OX40, GITR, or CD137.

Aspect 5. The method of aspect 1 or 2, wherein the immune checkpoint inhibitor is a CD96 inhibitor.

Aspect 6. The method of aspect 1 or 2, wherein the immune checkpoint inhibitor is a PD-1 inhibitor.

Aspect 7. The method of aspect 6, wherein the PD-1 inhibitor is an anti-PD-1 monoclonal antibody.

Aspect 8. The method of aspect 7, wherein the anti-PD-1 monoclonal antibody is nivolumab, pembrolizumab, pidilizumab, SHR-1210, PDR001, or AMP-224.

Aspect 9. The method of aspect 7 or 8, wherein the anti-PD-1 monoclonal antibody is nivolumab or pembrolizumab.

Aspect 10. The method of aspect 1 or 2, wherein the immune checkpoint inhibitor is a PD-L1 inhibitor.

Aspect 11. The method of aspect 10, wherein the PD-L1 inhibitor is an anti-PD-L1 monoclonal antibody.

Aspect 12. The method of aspect 11, wherein the anti-PD-L1 monoclonal antibody is atezolizumab, avelumab, durvalumab, BMS-935559, MEDI4736, MPDL3280A, or MSB0010718C.

Aspect 13. The method of aspect 1, wherein the immune checkpoint inhibitor is a CTLA-4 inhibitor.

Aspect 14. The method of aspect 13, wherein CTLA-4 inhibitor is an anti-CTLA-4 antibody.

Aspect 15. The method of aspect 14, wherein the anti-CTLA-4 antibody is ipilimumab.

Aspect 16. The method of aspect 1 or 2, wherein the immune checkpoint inhibitor is a LAG3 inhibitor.

Aspect 17. The method of aspect 16, wherein the LAG inhibitor is an anti-LAG3 antibody.

Aspect 18. The method of aspect 17, wherein the anti-LAG3 antibody is BMS-986016 or LAG525.

Aspect 19. The method of aspect 1 or 2, wherein the immune checkpoint inhibitor is a GITR inhibitor.

Aspect 20. The method of aspect 19, wherein the GITR inhibitor is an anti-GITR antibody.

Aspect 21. The method of aspect 20, wherein the anti-GITR antibody is TRX518, MK-4166, or INCAGN01876.

Aspect 22. The method of aspect 1 or 2, wherein the immune checkpoint inhibitor is an OX40 inhibitor.

Aspect 23. The method of aspect 22, wherein the OX40 inhibitor is an anti-OX40 antibody or OX40L fusion protein.

Aspect 24. The method of aspect 23, wherein the anti-OX40 antibody is MEDI0562 or INCAGN01949.

Aspect 25. The method of aspect 23, wherein the OX40L fusion protein is MEDI6383.

Aspect 26. The method of aspect 1 or 2, wherein the immune checkpoint inhibitor is TIM3 inhibitor.

Aspect 27. The method of aspect 26, wherein the TIM3 inhibitor is an anti-TIM3 antibody.

Aspect 28. The method of any one of the preceding aspects, further comprising administering a KIR inhibitor, TIGIT inhibitor, LAIR1 inhibitor, CD160 inhibitor, 2B4 inhibitor, TGFR beta inhibitor, or a combination thereof to the subject.

Aspect 29. The method of any one of the preceding aspects, wherein the compound is:

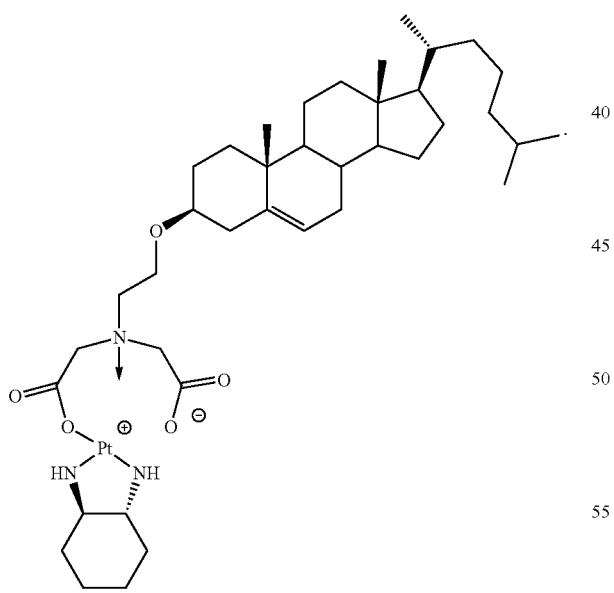

Aspect 30. The method of any one of the preceding aspects, wherein the compound and immune checkpoint inhibitor are administered separately.

Aspect 31. The method of any one of aspects 1 to 29, wherein the compound and immune checkpoint inhibitor are administered simultaneously.

Aspect 32. The method of any one of the preceding aspects, wherein the cancer is prostate cancer, colorectal cancer, pancreatic cancer, cervical cancer, stomach cancer, endometrial cancer, brain cancer, liver cancer, bladder cancer, ovarian cancer, testicle cancer, head cancer, neck cancer, skin cancer such as melanoma or basal carcinoma, mesothelial lining cancer, white blood cell cancer such as lymphoma or leukaemia, esophagael cancer, breast cancer, muscle cancer, connective tissue cancer, lung cancer such as small-cell lung carcinoma or non-small-cell carcinoma, adrenal gland cancer, thyroid cancer, kidney cancer, or bone cancer.

Aspect 33. A pharmaceutical composition comprising:

(i) a compound of the following structure, or a pharmaceutically acceptable salt thereof,

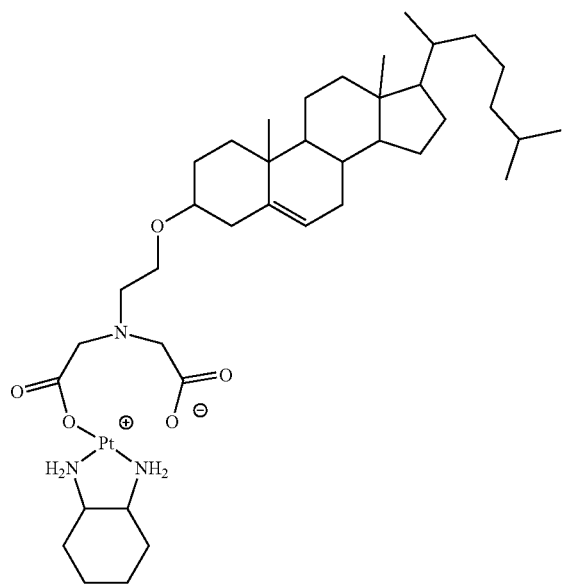

(IO-125)

(ii) an immune checkpoint inhibitor; and (iii) a pharmaceutically acceptable excipient.

Aspect 34. The pharmaceutical composition of aspect 33, wherein the immune checkpoint inhibitor is an inhibitor against A2AR, arginase, B7-H3, B7-H4, BTLA, CD47, CD73, CD96, CSF1R, CTLA-4, JAK, LAG3, P13K delta, P13K gamma, PD-1, PD-L1, PD-L2, TAM, TIM3, VISTA, a stimulatory checkpoint molecule, or a combination thereof.

Aspect 35. The pharmaceutical composition of aspect 34, wherein the JAK immune checkpoint inhibitor is a JAKI inhibitor, JAK2 inhibitor, or a combination thereof.

Aspect 36. The pharmaceutical composition of aspect 34, wherein the stimulatory checkpoint molecule is CD27, CD28, CD40, CD122, ICOS, OX40, GITR, or CD137.

Aspect 37. The pharmaceutical composition of aspect 33 or 34, wherein the immune checkpoint inhibitor is a CD96 inhibitor.

Aspect 38. The pharmaceutical composition of aspect 33 or 34, wherein the immune checkpoint inhibitor is a PD-1 inhibitor.

Aspect 39. The pharmaceutical composition of aspect 38, wherein the PD-1 inhibitor is an anti-PD-1 monoclonal antibody.

Aspect 40. The pharmaceutical composition of aspect 39, wherein the anti-PD-1 monoclonal antibody is nivolumab, pembrolizumab, pidilizumab, SHR-1210, PDR001, or AMP-224.

Aspect 41. The pharmaceutical composition of aspect 39 or 40, wherein the anti-PD-1 monoclonal antibody is nivolumab or pembrolizumab.

Aspect 42. The pharmaceutical composition of aspect 39 or 40, wherein the immune checkpoint inhibitor is a PD-L1 inhibitor.

Aspect 43. The pharmaceutical composition of aspect 42, wherein the PD-L1 inhibitor is an anti-PD-L1 monoclonal antibody.

Aspect 44. The pharmaceutical composition of aspect 43, wherein the anti-PD-L1 monoclonal antibody is atezolizumab, avelumab, durvalumab, BMS-935559, MEDI4736, MPDL3280A, or MSB0010718C.

Aspect 45. The pharmaceutical composition of aspect 33, wherein the immune checkpoint inhibitor is a CTLA-4 inhibitor.

Aspect 46. The pharmaceutical composition of aspect 45, wherein CTLA-4 inhibitor is an anti-CTLA-4 antibody.

Aspect 47. The pharmaceutical composition of aspect 46, wherein the anti-CTLA-4 antibody is ipilimumab.

Aspect 48. The pharmaceutical composition of aspect 33 or 34, wherein the immune checkpoint inhibitor is a LAG3 inhibitor.

Aspect 49. The pharmaceutical composition of aspect 48, wherein the LAG inhibitor is an anti-LAG3 antibody.

Aspect 50. The pharmaceutical composition of aspect 49, wherein the anti-LAG3 antibody is BMS-986016 or LAG525.

Aspect 51. The pharmaceutical composition of aspect 33 or 34, wherein the immune checkpoint inhibitor is a GITR inhibitor.

Aspect 52. The pharmaceutical composition of aspect 51, wherein the GITR inhibitor is an anti-GITR antibody.

Aspect 53. The pharmaceutical composition of aspect 52, wherein the anti-GITR antibody is TRX518, MK-4166, or INCAGN01876.

Aspect 54. The pharmaceutical composition of aspect 33 or 34, wherein the immune checkpoint inhibitor is an OX40 inhibitor.

Aspect 55. The pharmaceutical composition of aspect 54, wherein the OX40 inhibitor is an anti-OX40 antibody or OX40L fusion protein.

Aspect 56. The pharmaceutical composition of aspect 55, wherein the anti-OX40 antibody is MED10562 or INCAGN01949.

Aspect 57. The pharmaceutical composition of aspect 55, wherein the OX40L fusion protein is MED16383.

Aspect 58. The pharmaceutical composition of aspect 33 or 34, wherein the immune checkpoint inhibitor is TIM3 inhibitor.

Aspect 59. The pharmaceutical composition of aspect 58, wherein the TIM3 inhibitor is an anti-TIM3 antibody.

Aspect 60. The pharmaceutical composition of any one of aspects 33 to 59, further comprising a KIR inhibitor, TIGIT inhibitor, LAIR1 inhibitor, CD160 inhibitor, 2B4 inhibitor, TGFR beta inhibitor, or a combination thereof.

Aspect 61. The pharmaceutical composition of any one of aspects 1 to 60, wherein the compound is:

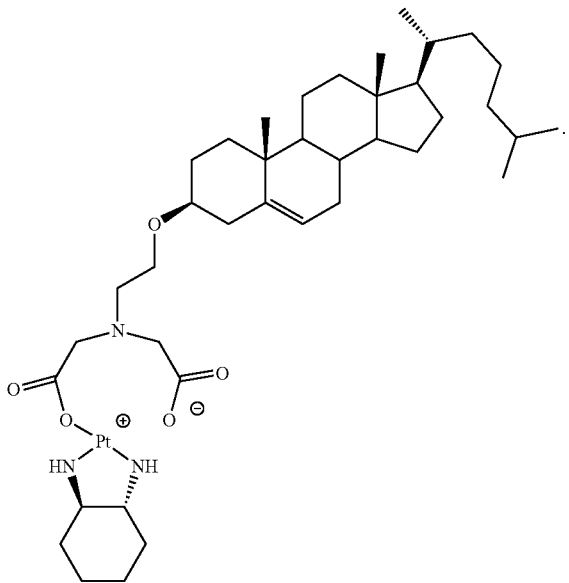

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees c., pressure is at or near atmospheric.

EXAMPLES

Example 1: Combinatorial Effect on Lung Cancer

The combination of a PD1 immune checkpoint inhibitor and IO-125 was evaluated in an immunocompetent murine NSCLS tumor model. The murine NSCLC tumor model was generated by subcutaneously implanting LLC cells in C57/BL6 mice. Treatment with saline (control), IO-125, immune check point inhibitor (anti-PD1 antibody, Biolegend) or combinatorial therapy (IO-125 and anti-PD1 antibody) was initiated when average tumor volume in the animals reached 100 mm$^3$, through i.v. administration of compounds. A schematic representation of the treatment regimen is depicted in FIG. 1A.

Figure 1:
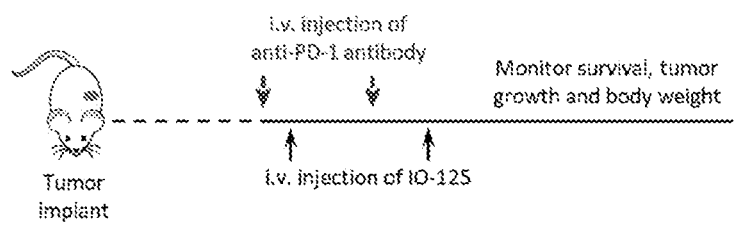
FIG. 1A is a schematic representation of study to evaluate combinatorial effect of IO-125 and immune checkpoint inhibitor. A tabular representation of dosage and dosing regimen is shown alongside.
FIG. 1B is a bar graph showing combinatorial treatment using IO-125 and immune checkpoint inhibitor (anti-PDI antibody), which resulted in efficient tumor volume reduction on comparison to monotherapies using either anti-PDI or IO-125.
Figure 1:
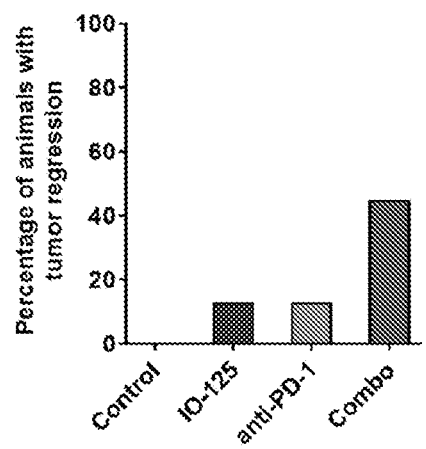
Figure 2:
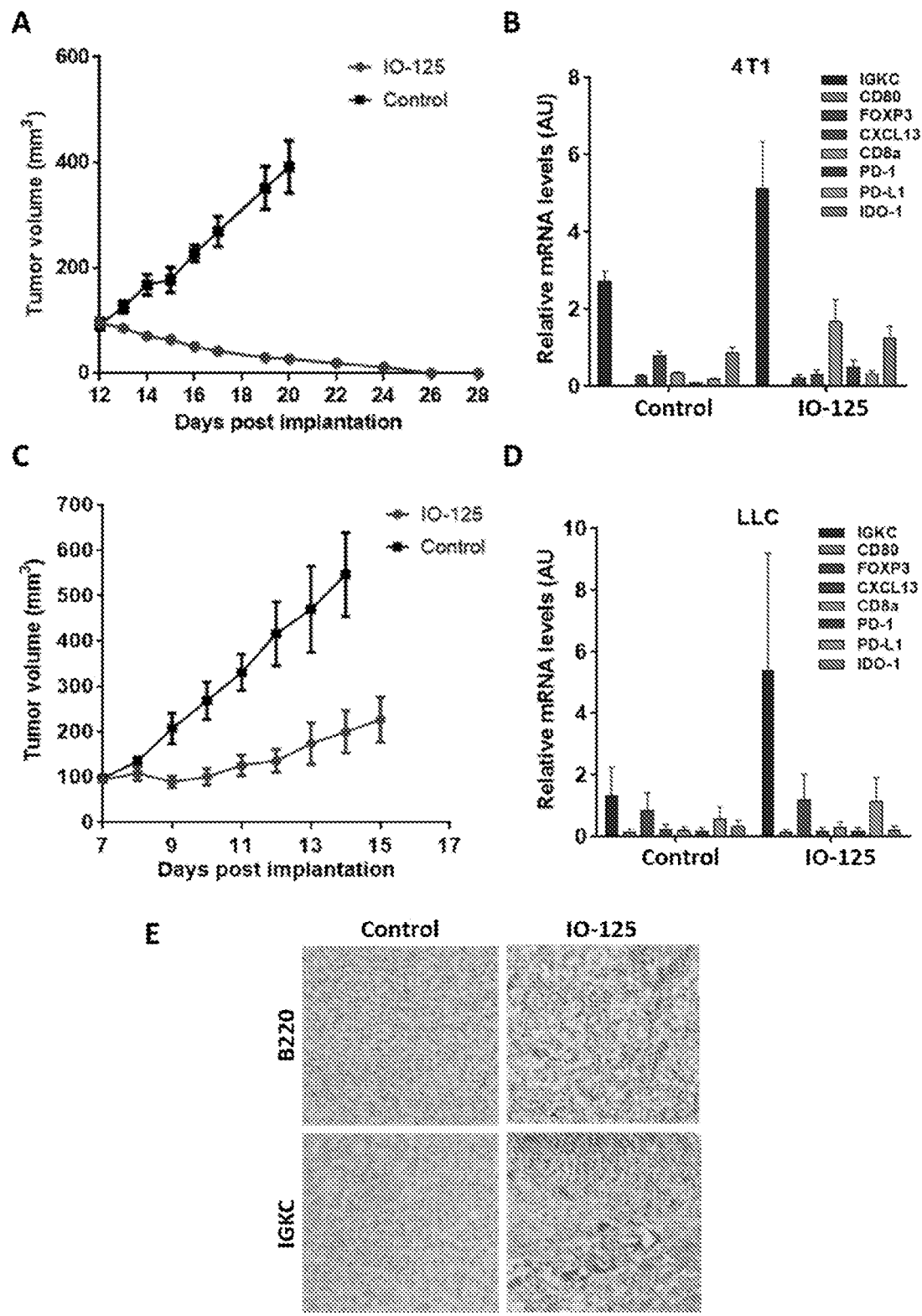
FIG. 2A shows tumor growth curves of syngeneic breast cancer (4T1) bearing animal that were treated with two cycles of IO-125 or saline. IO-125 resulted in complete tumor regression in 4T1 tumor bearing animals.
FIG. 2B is a bar graph showing the relative expression of different immune biomarkers that correlate with survival in breast cancer patients. IGKC is a biomarker for B cell activation.
FIG. 2C depicts tumor growth curves showing significant tumor growth inhibition but no regression in syngeneic lung cancer (LLC) bearing animals upon treatment with two cycles of IO-125.
FIG. 2D is a bar graph showing that molecular immunophenotyping revealed an increase in IGKC levels.
FIG. 2E are images of tumor sections from IO-125 treated or control tumors, showing immunodetection of B220 and IGKC. Treatment with IO-125 significantly increased expression of IGKC (a marker for matured B and plasma cells) in tumors.

This data showed that combinatorial treatment using IO-125 and the immune checkpoint inhibitor (anti-PD1 antibody) resulted in efficient tumor volume reduction in comparison to monotherapies using either anti-PD1 or IO-125 (FIG. 1B). Specifically, only 12.5% of the animals treated with IO-125 or PD1-inhibitor exhibited a complete regression of lung cancer. In contrast, 45% of the animals underwent complete tumor regression when the two drugs were combined. These observations illustrate that combinations of IO-125 with immune checkpoint inhibitor(s) augment tumor regression as compared to monotherapies. FIG. 2C shows significant tumor growth inhibition but no regression in lung cancer-bearing animals upon treatment with IO-125. The relative expressions of different immune biomarkers that correlate with survival in lung cancer patients were also measured (FIG. 2D), which illustrate an increase in IGKC levels in IO-125 treated animals.

Subsequently, tumors were harvested and a portion fixed in formalin. Immunohistochemical evaluation of FFPE sections from the fixed tumors showed elevated levels of IGKC and B220 (FIG. 2E), suggesting recruitment of humoral immune cells.

Example 2: Tumor Regression in Triple Negative Breast Cancers (TNBC)

The efficacy of IO-125 was examined in the murine triple negative breast cancer (TNBC) tumor model (4T1). 4T1 cells were subcutaneously implanted in Balb/c mice to generate tumors and treated with IO-125 or saline (control), when tumors reached an average volume of 100 mm$^3$. The dose administered for IO-125 was 20 mgPt/kg, with a regimen of b5d. Following one cycle of treatment, tumors were harvested and a portion of the tumor from control and IO-125 treated group was used for total RNA isolation and subsequent evaluation of immune activating and immune suppressive genes (Denkert et al., Clin Oncol. 2015; 33(9): 983-91) by semi-quantitative PCR. IO-125 treatment was continued for an additional cycle, with recording of tumor volume and examination of tumors for regression.

The tumor growth curve for 4T1 tumor-bearing animals showed that upon treatment with two cycles of IO-125, a complete regression of tumors was observed (FIG. 2A). The relative expressions of different immune biomarkers that correlate with survival in breast cancer patients were also measured. A significant increase in IGKC mRNA levels was observed in tumors treated with IO-125 (FIG. 2B).

Example 3: Tumor Rechallenge

Figure 3A:
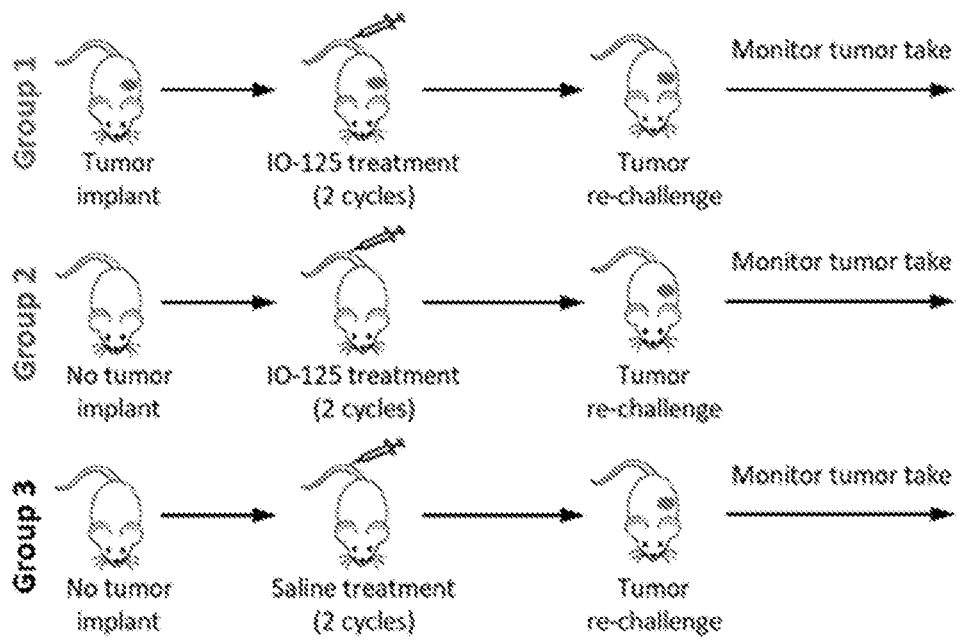
FIG. 3A is a schematic representation of immune memory study.

4T1 cells were subcutaneously implanted in Balb/c mice to generate tumors. When tumors reached an average volume of 100 mm$^3$, they were treated with IO-125 (Group 1). Two groups of Balb/c mice (non-tumor bearing) were either treated with IO-125 or saline (designated Group 2 and 3 respectively; FIG. 3A). The detailed study plan has been schematically shown in FIG. 3A. Immune memory cells are poised to rapidly expand and induce effector functions upon recurrence, while existing in a functionally quiescent state. To verify this hypothesis, we examined immune memory in IO-125 treated tumors.

Figure 3B:
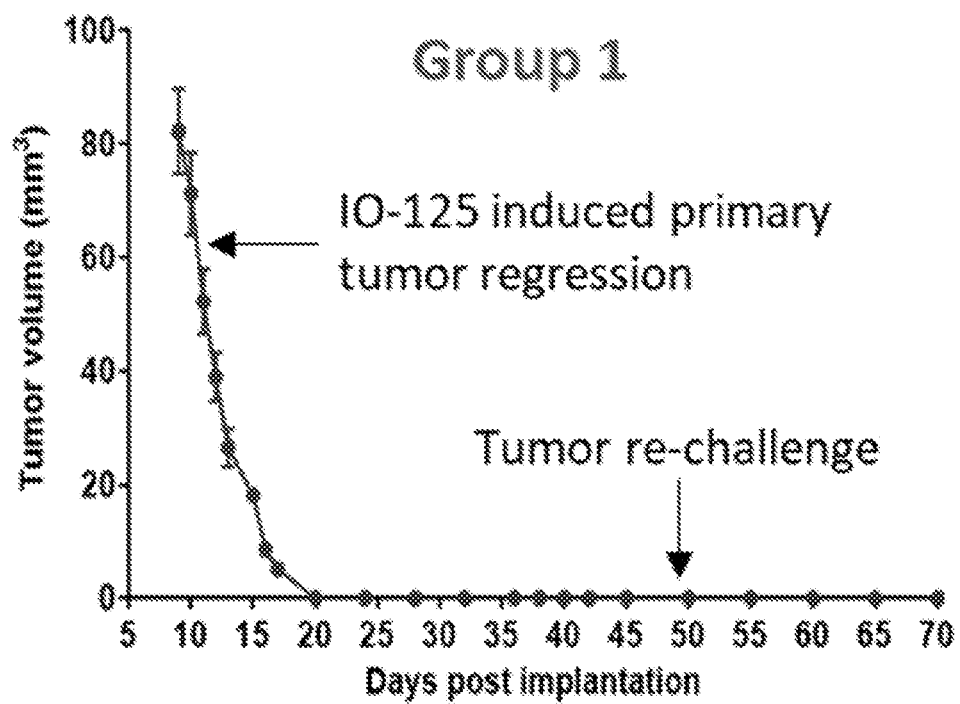
FIG. 3B is a line graph showing tumor regression following treatment with IO-125.
Figure 3C:
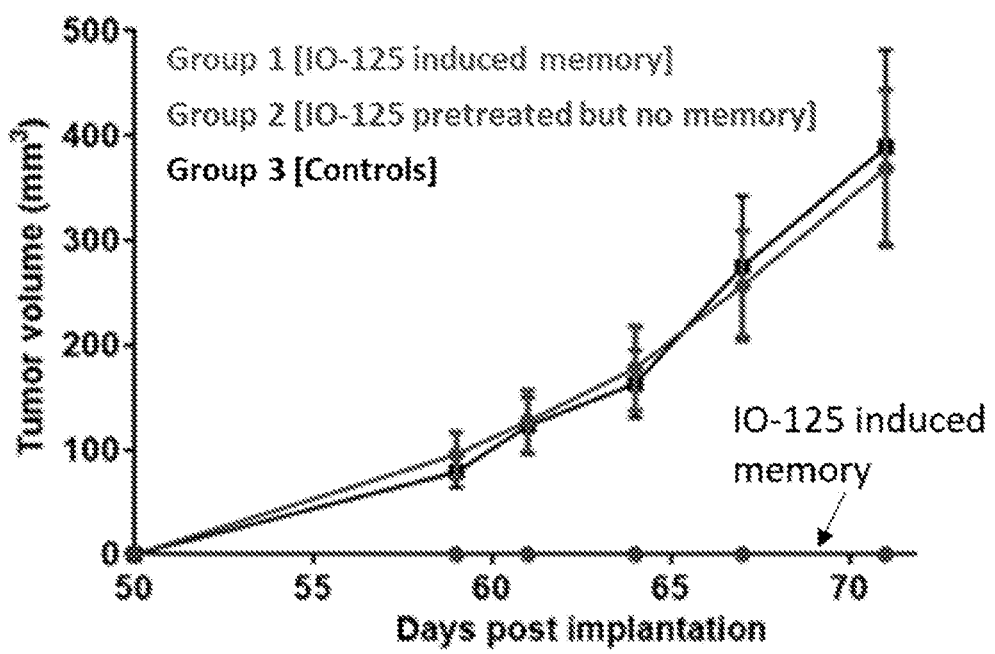
FIG. 3C is a line graph depicting growth of tumors across groups (classified in FIG. 3A) following tumor-rechallenge. No tumor growth occurred following re-implantation of cancer cells in animals which had previously undergone tumor regression with IO-125, which is consistent with immune memory.

Results indicated that treatment with IO-125 induced immune memory in treated animals, as no tumor growth was observed upon re-implantation of cancer cells into animals (Group 1), which had previously undergone tumor regression with IO-125 treatment (FIG. 3B). Non-tumor bearing Balb/c mice, treated with IO-125, when re-implanted with 4T1 cells led to the growth of tumors (Group 2), similar to those observed for saline treated mice (Group 3) (FIG. 3C). This example demonstrates the ability of the claimed compositions to prevent reoccurrence of cancer in mice, through the phenomenon of "immunological memory" and rules out the effect of any residual drug inducing tumor memory in non-tumor bearing animals.

Example 4: TLR Activation

Figure 4A:
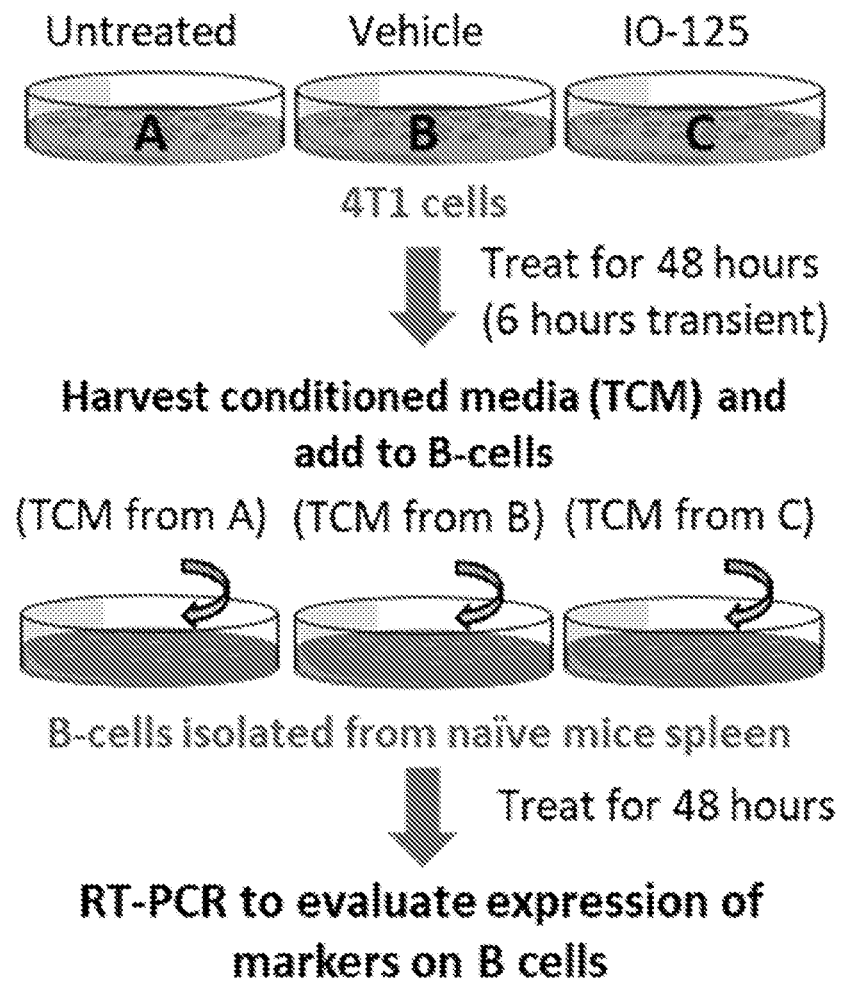
FIG. 4A is a schematic representation to study the role of 4TI conditioned media in TLR activation and differentiation of naïve splenic B-cells.

To evaluate the activation of TLRs leading to activation of B-cells, a study was designed as shown in FIG. 4A. 4T1 cells were seeded in cell culture dishes in IMDM media containing 10% FBS. The cells were treated with blank supramolecule (Vehicle) and IO-125 when they reached 60% confluence. Following a transient treatment of 6 hours, the media was removed and supplemented with fresh culture media and cells were incubated for additional 42 hours. Following treatment, the conditioned media from 4T1 cells (TCM) was collected for each treatment and filtered through 0.2 micron PES filters to obtain TCM free of cell debris. The harvested TCMs were used immediately for conditioning of B cells, isolated from naïve mice splenocytes using the EasySep Stem Cell B cell isolation kit as per manufacturers protocol. The B cells were incubated with conditioned media and harvested after 48 hours of incubation. RNA was isolated from the B cells and used for relative mRNA expression level evaluation of genes involved in B cell differentiation and TLR activation.

The results indicated that B cell differentiation markers and TLR activation markers were substantially increased in splenic B cells cultured with TCM from IO-125 treated 4T1 cells (FIG. 4B). This suggested that factor(s) secreted/released by 4T1 cells post treatment with IO-125 could activate TLRs, which in turn are immunostimulatory towards B cells.

These results prompted investigating the role of immune components in tumor regression following treatment with IO-125. Hence, we studied tumor regression in B cell-deficient mice (designated Jh$^{-/-}$) and mice lacking functional B cells and T cells (SCID). 4T1 cells were subcutaneously implanted in the mice strains mentioned and when tumors reached an average volume of 100 mm$^3$, they were divided into two groups. One group was kept as control and the other treated with IO-125 and tumor volume in all the animals were recorded. Tumor ablation did not occur in mice lacking B cells (FIGS. 4C and 4D), illustrating the role of B cell-mediated tumor regression upon treatment with IO-125.

Example 5: Insights into Mechanism(s) Underlying B Cell Activation

Splenic B cells were isolated from Group 1 and Group 2 mice, described in Example 3. A schematic representation of experimental detail in shown in FIG. 5A. Spleen was harvested from mice (n=3) and minced into small pieces in RPMI-1640 basal media. The pieces were placed on top of a 40 mesh membrane and crushed with the back of a syringe and the single cell suspension was collected onto a 50 mL tube. The single cell suspension was washed twice with PBS to remove debris by centrifuging at 2000 rpm. Splenocytes were counted using haemocytometer and 100 million splenocytes were resuspended in 1 mL of Isolation buffer (2% FBS, 100 mM EDTA in DPBS) and transferred to a 5 ml Polystyrene tube. The B cells were isolated from splenocytes using the EasySep Stem Cell B cell isolation kit as per manufacturers protocol. One part of the isolated B cells was used for RNA isolation, followed by relative mRNA expression levels of genes involved in B cell differentiation and TLR activation were evaluated; while the second part was used for immunodetection of specific proteins, following the manufacturer's protocol.

The results indicated a significant increase in IGKC mRNA levels in splenic B cells isolated from tumor bearing mice treated with IO-125 (FIG. 5B). An elevated expression of TLRs and CD80 was also noted in these mice.

In order to understand the mechanism underlying B cell activation, in addition to the TLRs, we also examined the B cell receptors (BCRs), where the translocation of NFkB to the nucleus is reported for activation of B cell differentiation machinery. As shown in FIG. 5C, B cells isolated from the spleen of tumor-bearing animals, treated with IO-125 show clustering of HMGB1 on the surface and nuclear translocation of NF-kB, as compared to control non-tumor naïve animals that were similarly treated with IO-125.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present disclosure contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A method of treating non-small cell lung cancer (NSCLC) in a subject in need thereof, comprising administering to the subject, compound IO-125:

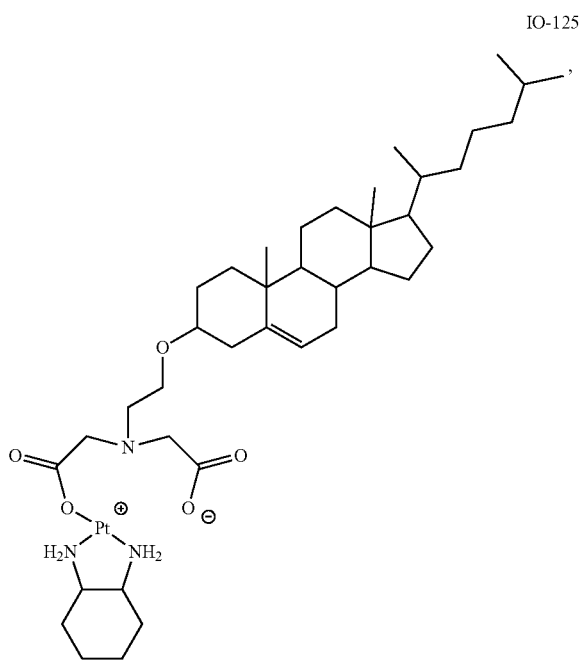

IO-125 or a pharmaceutically acceptable salt thereof, and an anti-PD-1 antibody.

2. The method of claim 1, wherein the compound IO-125 and anti-PD-1 antibody are administered separately.

3. The method of claim 1, wherein the compound IO-125 and anti-PD-1 antibody are administered simultaneously.

4. The method of claim 1, wherein the compound IO-125 is administered to the subject.

5. The method of claim 1, wherein the pharmaceutically acceptable salt of the compound IO-125 is administered to the subject.

6. The method of claim 1, wherein the anti-PD-1 antibody is a monoclonal antibody.

7. The method of claim 6, wherein the monoclonal antibody is nivolumab, pembrolizumab, pidilizumab, SHR-1210, PDR001, or AMP-224.

8. The method of claim 6, wherein the monoclonal antibody is nivolumab.

9. The method of claim 6, wherein the monoclonal antibody is pembrolizumab.

10. The method of claim 6, wherein the monoclonal antibody is pidilizumab.

11. The method of claim 6, wherein the monoclonal antibody is SHR-1210.

12. The method of claim 6, wherein the monoclonal antibody is PDR001.

13. The method of claim 6, wherein the monoclonal antibody is AMP-224.

14. The method of claim 1, wherein the administration is intravenous administration.

* * * * *